US008524476B2

(12) United States Patent
Smirnov et al.

(10) Patent No.: US 8,524,476 B2
(45) Date of Patent: Sep. 3, 2013

(54) BACTERIUM PRODUCING A PRODUCT OF A REACTION CATALYZED BY A PROTEIN HAVING 2-OXOGLUTARATE-DEPENDENT ENZYME ACTIVITY AND A METHOD FOR MANUFACTURING THE PRODUCT

(75) Inventors: Sergey Vasilievich Smirnov, Moscow (RU); Natalia Nikolaevna Samsonova, Moscow (RU); Veronika Aleksandrovna Kotliarova, Moscow (RU); Natalia Yurievna Rushkevich, Moscow (RU); Olga Sergeevna Beznoschenko, Stavropol territory (RU); Tatyana Aleksandrovna Bachina, Moscow region (RU); Yuki Imabayashi, Kawasaki (JP); Masakazu Sugiyama, Kawasaki (JP); Shunichi Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 393 days.

(21) Appl. No.: 12/819,485

(22) Filed: Jun. 21, 2010

(65) Prior Publication Data

US 2010/0330622 A1  Dec. 30, 2010

Related U.S. Application Data

(63) Continuation of application No. PCT/JP2008/073914, filed on Dec. 22, 2008.

(30) Foreign Application Priority Data

Dec. 21, 2007  (RU) ................................ 2007147436

(51) Int. Cl.
| C12N 9/02 | (2006.01) |
| C12N 1/20 | (2006.01) |
| C12N 15/00 | (2006.01) |
| C12P 13/06 | (2006.01) |
| C12P 1/04 | (2006.01) |
| C07H 21/04 | (2006.01) |

(52) U.S. Cl.
USPC ... 435/189; 435/116; 435/252.3; 435/252.32; 435/252.33; 435/320.1; 435/170; 536/23.2

(58) Field of Classification Search
None
See application file for complete search history.

(56) References Cited

U.S. PATENT DOCUMENTS

| 5,492,818 A | 2/1996 | Nakazawa et al. |
| 5,854,040 A | 12/1998 | Ozaki et al. |
| 7,138,266 B2 | 11/2006 | Debabov et al. |
| 7,354,746 B1 | 4/2008 | Suzuki et al. |
| 7,575,910 B2 | 8/2009 | Suzuki et al. |
| 7,670,822 B2 | 3/2010 | Smirnov et al. |
| 2005/0181488 A1 | 8/2005 | Akhverdian et al. |
| 2007/0212764 A1 | 9/2007 | Ptitsyn et al. |
| 2008/0241895 A1 | 10/2008 | Suzuki et al. |
| 2009/0203090 A1 | 8/2009 | Ptitsyn et al. |
| 2009/0275092 A1 | 11/2009 | Kodera et al. |

FOREIGN PATENT DOCUMENTS

| CN | 1533439 | 9/2004 |
| EP | 0 670 370 | 1/1995 |
| WO | WO03/008616 | 1/2003 |

OTHER PUBLICATIONS

Tauch et al. Isoleucine uptake in *Corynebacterium glutamicum* ATCC 13032 is directed by the brnQ gene product, Arch Microbiol (1998) 169: 303-312.*
Haefele et al. Characterization of a deoxygenase from *Trigonella foenum-graecum* involved in 4-hydroxyisoleucine biosynthesis, Phytochemistry (1997) 44(4): 563-566.*
Creaghan, I. T., et al., "Succinate Dehydrogenase-dependent Nutritional Requirement for Succinate in Mutants of *Escherichia coli* K12," J. Gen. Microbiol. 1978;107(1):1-13.
Rolland-Fulcrand, V., et al., "Chemoenzymatic Synthesis of Enantiomerically Pure (2S,3R,4S)-4-Hydroxy-isoleucine, an Insulinotropic Amino Acid Isolated from Fenugreek Seeds," Eur. J. Org. Chem. 2004:873-877.
International Search Report for PCT Patent App. No. PCT/JP2008/073914 (Mar. 31, 2009).
Written Opinion for PCT Patent App. No. PCT/JP2008/073914 (Mar. 31, 2009).
Hausinger, R. P., "Fe(H)/β-Ketoglutarate-Dependent Hydroxylases and Related Enzymes," Critical Rev. Biochem. Mol. Biol. 2004;39:21-68.
Loenarz, C., et al., "Expanding chemical biology of 2-oxoglutarate oxygenases," Nature Chem. Biol. 2008;4(3):152-156.
International Preliminary Report on Patentability for PCT Patent App. No. PCT/JP2008/073914 (Jul. 1, 2010).
Office Action issued in Chinese Patent App. No. 200880122135.8 (Aug. 30, 2011) with English translation thereof.

* cited by examiner

*Primary Examiner* — Anand Desai
*Assistant Examiner* — Iqbal H Chowdhury
(74) *Attorney, Agent, or Firm* — Shelly Guest Cermak; Cermak Nakajima LLP

(57) ABSTRACT

A method for manufacturing a product of a reaction catalyzed by a protein having 2-oxoglutarate-dependent enzyme activity such as (2S,3R,4S)-4-hydroxy-L-isoleucine or a salt thereof using a bacterium transformed with a DNA fragment containing a gene coding for a protein having 2-oxoglutarate-dependent enzyme activity such as L-isoleucine dioxygenase activity; and wherein said bacterium has the ability to produce a product such as (2S,3R,4S)-4-hydroxy-L-isoleucine.

12 Claims, 4 Drawing Sheets

SEQUENCE LISTING

<160> NUMBER OF SEQ ID NOS: 40

<210> SEQ ID NO 1
<211> LENGTH: 717
<212> TYPE: DNA
<213> ORGANISM: Bacillus thuringiensis strain FERM BP-10688
<220> FEATURE:
<221> NAME/KEY: CDS
<222> LOCATION: (1)..(717)

<400> SEQUENCE: 1

| aaa | atg | agt | ggc | ttt | agc | ata | gaa | gaa | aag | gta | cat | gaa | ttt | gaa | tct | 48 |
|---|---|---|---|---|---|---|---|---|---|---|---|---|---|---|---|---|
| Lys | Met | Ser | Gly | Phe | Ser | Ile | Glu | Glu | Lys | Val | His | Glu | Phe | Glu | Ser | |
| 1 | | | | 5 | | | | | 10 | | | | | 15 | | |

| aaa | ggg | ttt | ctt | gaa | atc | tca | aat | gaa | atc | ttt | tta | caa | gag | gaa | gag | 96 |
|---|---|---|---|---|---|---|---|---|---|---|---|---|---|---|---|---|
| Lys | Gly | Phe | Leu | Glu | Ile | Ser | Asn | Glu | Ile | Phe | Leu | Gln | Glu | Glu | Glu | |
| | | | | 20 | | | | | 25 | | | | | 30 | | |

| aat | cat | agt | tta | tta | aca | caa | gca | cag | tta | gat | tat | tat | aat | ttg | gaa | 144 |
|---|---|---|---|---|---|---|---|---|---|---|---|---|---|---|---|---|
| Asn | His | Ser | Leu | Leu | Thr | Gln | Ala | Gln | Leu | Asp | Tyr | Tyr | Asn | Leu | Glu | |
| | | 35 | | | | | 40 | | | | | 45 | | | | |

| gat | gat | gcg | tac | ggt | gaa | tgc | cgt | gct | aga | tct | tat | tca | agg | tat | ata | 192 |
|---|---|---|---|---|---|---|---|---|---|---|---|---|---|---|---|---|
| Asp | Asp | Ala | Tyr | Gly | Glu | Cys | Arg | Ala | Arg | Ser | Tyr | Ser | Arg | Tyr | Ile | |
| 50 | | | | | 55 | | | | | 60 | | | | | | |

| aag | tat | gtt | gat | tca | cca | gat | tat | att | tta | gat | aat | agt | aat | gat | tac | 240 |
|---|---|---|---|---|---|---|---|---|---|---|---|---|---|---|---|---|
| Lys | Tyr | Val | Asp | Ser | Pro | Asp | Tyr | Ile | Leu | Asp | Asn | Ser | Asn | Asp | Tyr | |
| 65 | | | | | 70 | | | | | 75 | | | | | 80 | |

| ttc | caa | tct | aaa | gaa | tat | aac | tat | gat | gat | ggc | ggg | aaa | gtt | aga | cag | 288 |
|---|---|---|---|---|---|---|---|---|---|---|---|---|---|---|---|---|
| Phe | Gln | Ser | Lys | Glu | Tyr | Asn | Tyr | Asp | Asp | Gly | Gly | Lys | Val | Arg | Gln | |
| | | | | 85 | | | | | 90 | | | | | 95 | | |

| ttc | aat | agc | ata | aat | gat | agc | ttt | tta | tgt | aat | cct | tta | att | caa | aat | 336 |
|---|---|---|---|---|---|---|---|---|---|---|---|---|---|---|---|---|
| Phe | Asn | Ser | Ile | Asn | Asp | Ser | Phe | Leu | Cys | Asn | Pro | Leu | Ile | Gln | Asn | |
| | | | 100 | | | | | 105 | | | | | 110 | | | |

| atc | gtg | cgt | ttc | gat | act | gag | ttt | gca | ttt | aaa | aca | aat | ata | ata | gat | 384 |
|---|---|---|---|---|---|---|---|---|---|---|---|---|---|---|---|---|
| Ile | Val | Arg | Phe | Asp | Thr | Glu | Phe | Ala | Phe | Lys | Thr | Asn | Ile | Ile | Asp | |
| | | | 115 | | | | | 120 | | | | | 125 | | | |

| aaa | agt | aaa | gat | tta | att | ata | ggc | tta | cat | caa | gta | aga | tat | aaa | gct | 432 |
|---|---|---|---|---|---|---|---|---|---|---|---|---|---|---|---|---|
| Lys | Ser | Lys | Asp | Leu | Ile | Ile | Gly | Leu | His | Gln | Val | Arg | Tyr | Lys | Ala | |
| | 130 | | | | | 135 | | | | | 140 | | | | | |

| act | aaa | gaa | aga | cca | tct | ttt | agt | tca | cct | att | tgg | tta | cat | aaa | gat | 480 |
|---|---|---|---|---|---|---|---|---|---|---|---|---|---|---|---|---|
| Thr | Lys | Glu | Arg | Pro | Ser | Phe | Ser | Ser | Pro | Ile | Trp | Leu | His | Lys | Asp | |
| 145 | | | | | 150 | | | | | 155 | | | | | 160 | |

| gat | gaa | cca | gta | gta | ttt | tta | cac | ctt | atg | aat | tta | agt | aat | aca | gct | 528 |
|---|---|---|---|---|---|---|---|---|---|---|---|---|---|---|---|---|
| Asp | Glu | Pro | Val | Val | Phe | Leu | His | Leu | Met | Asn | Leu | Ser | Asn | Thr | Ala | |
| | | | | 165 | | | | | 170 | | | | | 175 | | |

| atc | ggc | gga | gat | aat | tta | ata | gct | aat | tct | cct | cgg | gaa | att | aat | cag | 576 |
|---|---|---|---|---|---|---|---|---|---|---|---|---|---|---|---|---|
| Ile | Gly | Gly | Asp | Asn | Leu | Ile | Ala | Asn | Ser | Pro | Arg | Glu | Ile | Asn | Gln | |
| | | | 180 | | | | | 185 | | | | | 190 | | | |

| ttt | ata | agt | ttg | aag | gag | cct | tta | gaa | act | tta | gta | ttt | gga | caa | aag | 624 |
|---|---|---|---|---|---|---|---|---|---|---|---|---|---|---|---|---|
| Phe | Ile | Ser | Leu | Lys | Glu | Pro | Leu | Glu | Thr | Leu | Val | Phe | Gly | Gln | Lys | |
| | | | 195 | | | | | 200 | | | | | 205 | | | |

| gtc | ttc | cat | gcc | gta | acg | cca | ctt | gga | aca | gaa | tgt | agt | acg | gag | gct | 672 |
|---|---|---|---|---|---|---|---|---|---|---|---|---|---|---|---|---|
| Val | Phe | His | Ala | Val | Thr | Pro | Leu | Gly | Thr | Glu | Cys | Ser | Thr | Glu | Ala | |
| | | 210 | | | | | 215 | | | | | 220 | | | | |

| ttt | cgt | gat | att | tta | tta | gta | aca | ttt | tct | tat | aag | gag | aca | aaa | | 717 |
|---|---|---|---|---|---|---|---|---|---|---|---|---|---|---|---|---|
| Phe | Arg | Asp | Ile | Leu | Leu | Val | Thr | Phe | Ser | Tyr | Lys | Glu | Thr | Lys | | |
| 225 | | | | | 230 | | | | | 235 | | | | | | |

<210> SEQ ID NO 2
<211> LENGTH: 239
<212> TYPE: PRT
<213> ORGANISM: Bacillus thuringiensis strain FERM BP-10688

<400> SEQUENCE: 2

```
Lys Met Ser Gly Phe Ser Ile Glu Glu Lys Val His Glu Phe Glu Ser
1               5                   10                  15
Lys Gly Phe Leu Glu Ile Ser Asn Glu Ile Phe Leu Gln Glu Glu Glu
                20                  25                  30
Asn His Ser Leu Leu Thr Gln Ala Gln Leu Asp Tyr Tyr Asn Leu Glu
            35                  40                  45
Asp Asp Ala Tyr Gly Glu Cys Arg Ala Arg Ser Tyr Ser Arg Tyr Ile
50                  55                  60
Lys Tyr Val Asp Ser Pro Asp Tyr Ile Leu Asp Asn Ser Asn Asp Tyr
65                  70                  75                  80
Phe Gln Ser Lys Glu Tyr Asn Tyr Asp Asp Gly Gly Lys Val Arg Gln
                85                  90                  95
Phe Asn Ser Ile Asn Asp Ser Phe Leu Cys Asn Pro Leu Ile Gln Asn
            100                 105                 110
Ile Val Arg Phe Asp Thr Glu Phe Ala Phe Lys Thr Asn Ile Ile Asp
        115                 120                 125
Lys Ser Lys Asp Leu Ile Ile Gly Leu His Gln Val Arg Tyr Lys Ala
    130                 135                 140
Thr Lys Glu Arg Pro Ser Phe Ser Ser Pro Ile Trp Leu His Lys Asp
145                 150                 155                 160
Asp Glu Pro Val Val Phe Leu His Leu Met Asn Leu Ser Asn Thr Ala
                165                 170                 175
Ile Gly Gly Asp Asn Leu Ile Ala Asn Ser Pro Arg Glu Ile Asn Gln
            180                 185                 190
Phe Ile Ser Leu Lys Glu Pro Leu Glu Thr Leu Val Phe Gly Gln Lys
        195                 200                 205
Val Phe His Ala Val Thr Pro Leu Gly Thr Glu Cys Ser Thr Glu Ala
    210                 215                 220
Phe Arg Asp Ile Leu Leu Val Thr Phe Ser Tyr Lys Glu Thr Lys
225                 230                 235
```

<210> SEQ ID NO 3
<211> LENGTH: 1320
<212> TYPE: DNA
<213> ORGANISM: Escherichia coli
<220> FEATURE:
<221> NAME/KEY: CDS
<222> LOCATION: (1)..(1320)

<400> SEQUENCE: 3

```
atg acc cat caa tta aga tcg cgc gat atc atc gct ctg ggc ttt atg      48
Met Thr His Gln Leu Arg Ser Arg Asp Ile Ile Ala Leu Gly Phe Met
1               5                   10                  15 aca ttt gcg ttg ttc gtc ggc gca ggt aac att att ttc cct cca atg      96
Thr Phe Ala Leu Phe Val Gly Ala Gly Asn Ile Ile Phe Pro Pro Met
                20                  25                  30 gtc ggc tta cag gca ggc gaa cac gtc tgg act gcg gca ttc ggc ttc     144
Val Gly Leu Gln Ala Gly Glu His Val Trp Thr Ala Ala Phe Gly Phe
            35                  40                  45 ctc att act gcc gtt ggc ctg ccg gta tta acg gta gtg gcg ctg gca     192
Leu Ile Thr Ala Val Gly Leu Pro Val Leu Thr Val Val Ala Leu Ala
50                  55                  60 aaa gtt ggc ggc ggt gtt gac agc ctc agc acg cca atc ggt aaa gtc     240
Lys Val Gly Gly Gly Val Asp Ser Leu Ser Thr Pro Ile Gly Lys Val
65                  70                  75                  80 gct ggc gta ctg ctg gca acg gtt tgt tac ctg gcg gtg ggg ccg ctt     288
```

```
Ala Gly Val Leu Leu Ala Thr Val Cys Tyr Leu Ala Val Gly Pro Leu
            85                  90                  95 ttc gct acg ccg cgt aca gct acc gtt tcc ttt gaa gtg ggg att gcg    336
Phe Ala Thr Pro Arg Thr Ala Thr Val Ser Phe Glu Val Gly Ile Ala
            100                 105                 110 ccg ctg acg ggt gat tcc gcg ctg ccg ctg ttt atc tac agc ctg gtc    384
Pro Leu Thr Gly Asp Ser Ala Leu Pro Leu Phe Ile Tyr Ser Leu Val
            115                 120                 125 tat ttc gct atc gtt att ctg gtt tcg ctc tat ccg ggc aag ctg ctg    432
Tyr Phe Ala Ile Val Ile Leu Val Ser Leu Tyr Pro Gly Lys Leu Leu
            130                 135                 140 gat acc gtg ggc aac ttc ctt gcg ccg ctg aaa att atc gcg ctg gtc    480
Asp Thr Val Gly Asn Phe Leu Ala Pro Leu Lys Ile Ile Ala Leu Val
145                 150                 155                 160 atc ctg tct gtt gcc gct att gtc tgg ccg gcg ggt tct atc agc acg    528
Ile Leu Ser Val Ala Ala Ile Val Trp Pro Ala Gly Ser Ile Ser Thr
                165                 170                 175 gcg act gag gct tat caa aac gct gcg ttt tct aac ggc ttc gtt aac    576
Ala Thr Glu Ala Tyr Gln Asn Ala Ala Phe Ser Asn Gly Phe Val Asn
            180                 185                 190 ggc tat ctg acc atg gat acg ctg ggc gca atg gtg ttt ggt atc gtt    624
Gly Tyr Leu Thr Met Asp Thr Leu Gly Ala Met Val Phe Gly Ile Val
            195                 200                 205 att gtt aac gcg gcg cgt tct cgt ggc gtt acc gaa gcg cgt ctg ctg    672
Ile Val Asn Ala Ala Arg Ser Arg Gly Val Thr Glu Ala Arg Leu Leu
            210                 215                 220 acc cgt tat acc gtc tgg gct ggc ctg atg gcg ggt gtt ggt ctg act    720
Thr Arg Tyr Thr Val Trp Ala Gly Leu Met Ala Gly Val Gly Leu Thr
225                 230                 235                 240 ctg ctg tac ctg gcg ctg ttc cgt ctg ggg tca gac agc gcg tcg ctg    768
Leu Leu Tyr Leu Ala Leu Phe Arg Leu Gly Ser Asp Ser Ala Ser Leu
                245                 250                 255 gtc gat cag tct gca aac ggc gct gct att ctg cat gct tac gtt cag    816
Val Asp Gln Ser Ala Asn Gly Ala Ala Ile Leu His Ala Tyr Val Gln
            260                 265                 270 cac acc ttt ggc ggc ggc ggt agc ttc ctg ctg gcg gcg tta atc ttc    864
His Thr Phe Gly Gly Gly Gly Ser Phe Leu Leu Ala Ala Leu Ile Phe
            275                 280                 285 atc gcc tgc ctg gta acg gca gtt ggc ctg acc tgt gct tgt gca gaa    912
Ile Ala Cys Leu Val Thr Ala Val Gly Leu Thr Cys Ala Cys Ala Glu
            290                 295                 300 ttc ttt gcc cag tac gta ccg ctc tct tat cgt acg ctg gtg ttt atc    960
Phe Phe Ala Gln Tyr Val Pro Leu Ser Tyr Arg Thr Leu Val Phe Ile
305                 310                 315                 320 ctc ggc ggc ttc tcg atg gtg gtt tct aac ctc ggc tta agc cag ctg    1008
Leu Gly Gly Phe Ser Met Val Val Ser Asn Leu Gly Leu Ser Gln Leu
            325                 330                 335 atc cag atc tcc gta ccg gtg ctg acc gct att tat ccg ccg tgt atc    1056
Ile Gln Ile Ser Val Pro Val Leu Thr Ala Ile Tyr Pro Pro Cys Ile
            340                 345                 350 gca ctg gtt gta tta agt ttt aca cgc tca tgg tgg cat aat tcg tcc    1104
Ala Leu Val Val Leu Ser Phe Thr Arg Ser Trp Trp His Asn Ser Ser
            355                 360                 365 cgc gtg att gct ccg ccg atg ttt atc agc ctg ctt ttt ggt att ctc    1152
Arg Val Ile Ala Pro Pro Met Phe Ile Ser Leu Leu Phe Gly Ile Leu
            370                 375                 380 gac ggg atc aaa gca tct gca ttc agc gat atc tta ccg tcc tgg gcg    1200
Asp Gly Ile Lys Ala Ser Ala Phe Ser Asp Ile Leu Pro Ser Trp Ala
385                 390                 395                 400 cag cgt tta ccg ctg gcc gaa caa ggt ctg gcg tgg tta atg cca aca    1248
```

```
                Gln Arg Leu Pro Leu Ala Glu Gln Gly Leu Ala Trp Leu Met Pro Thr
                            405                 410                 415 gtg gtg atg gtg gtt ctg gcc att atc tgg gat cgc gcg gca ggt cgt          1296
Val Val Met Val Val Leu Ala Ile Ile Trp Asp Arg Ala Ala Gly Arg
            420                 425                 430 cag gtg acc tcc agc gct cac taa                                          1320
Gln Val Thr Ser Ser Ala His
        435

<210> SEQ ID NO 4
<211> LENGTH: 439
<212> TYPE: PRT
<213> ORGANISM: Escherichia coli

<400> SEQUENCE: 4

Met Thr His Gln Leu Arg Ser Arg Asp Ile Ile Ala Leu Gly Phe Met
1               5                   10                  15

Thr Phe Ala Leu Phe Val Gly Ala Gly Asn Ile Ile Phe Pro Pro Met
            20                  25                  30

Val Gly Leu Gln Ala Gly Glu His Val Trp Thr Ala Ala Phe Gly Phe
        35                  40                  45

Leu Ile Thr Ala Val Gly Leu Pro Val Leu Thr Val Val Ala Leu Ala
    50                  55                  60

Lys Val Gly Gly Gly Val Asp Ser Leu Ser Thr Pro Ile Gly Lys Val
65                  70                  75                  80

Ala Gly Val Leu Leu Ala Thr Val Cys Tyr Leu Ala Val Gly Pro Leu
                85                  90                  95

Phe Ala Thr Pro Arg Thr Ala Thr Val Ser Phe Glu Val Gly Ile Ala
            100                 105                 110

Pro Leu Thr Gly Asp Ser Ala Leu Pro Leu Phe Ile Tyr Ser Leu Val
        115                 120                 125

Tyr Phe Ala Ile Val Ile Leu Val Ser Leu Tyr Pro Gly Lys Leu Leu
    130                 135                 140

Asp Thr Val Gly Asn Phe Leu Ala Pro Leu Lys Ile Ile Ala Leu Val
145                 150                 155                 160

Ile Leu Ser Val Ala Ala Ile Val Trp Pro Ala Gly Ser Ile Ser Thr
                165                 170                 175

Ala Thr Glu Ala Tyr Gln Asn Ala Ala Phe Ser Asn Gly Phe Val Asn
            180                 185                 190

Gly Tyr Leu Thr Met Asp Thr Leu Gly Ala Met Val Phe Gly Ile Val
        195                 200                 205

Ile Val Asn Ala Ala Arg Ser Arg Gly Val Thr Glu Ala Arg Leu Leu
    210                 215                 220

Thr Arg Tyr Thr Val Trp Ala Gly Leu Met Ala Gly Val Gly Leu Thr
225                 230                 235                 240

Leu Leu Tyr Leu Ala Leu Phe Arg Leu Gly Ser Asp Ser Ala Ser Leu
                245                 250                 255

Val Asp Gln Ser Ala Asn Gly Ala Ala Ile Leu His Ala Tyr Val Gln
            260                 265                 270

His Thr Phe Gly Gly Gly Ser Phe Leu Leu Ala Ala Leu Ile Phe
        275                 280                 285

Ile Ala Cys Leu Val Thr Ala Val Gly Leu Thr Cys Ala Cys Ala Glu
    290                 295                 300

Phe Phe Ala Gln Tyr Val Pro Leu Ser Tyr Arg Thr Leu Val Phe Ile
305                 310                 315                 320

Leu Gly Gly Phe Ser Met Val Val Ser Asn Leu Gly Leu Ser Gln Leu
```

```
                        325                 330                 335
Ile Gln Ile Ser Val Pro Val Leu Thr Ala Ile Tyr Pro Pro Cys Ile
                340                 345                 350

Ala Leu Val Val Leu Ser Phe Thr Arg Ser Trp Trp His Asn Ser Ser
            355                 360                 365

Arg Val Ile Ala Pro Pro Met Phe Ile Ser Leu Leu Phe Gly Ile Leu
        370                 375                 380

Asp Gly Ile Lys Ala Ser Ala Phe Ser Asp Ile Leu Pro Ser Trp Ala
385                 390                 395                 400

Gln Arg Leu Pro Leu Ala Glu Gln Gly Leu Ala Trp Leu Met Pro Thr
                405                 410                 415

Val Val Met Val Val Leu Ala Ile Ile Trp Asp Arg Ala Ala Gly Arg
            420                 425                 430

Gln Val Thr Ser Ser Ala His
        435

<210> SEQ ID NO 5
<211> LENGTH: 2802
<212> TYPE: DNA
<213> ORGANISM: Escherichia coli
<220> FEATURE:
<221> NAME/KEY: CDS
<222> LOCATION: (1)..(2802)

<400> SEQUENCE: 5 atg cag aac agc gct ttg aaa gcc tgg ttg gac tct tct tac ctc tct     48
Met Gln Asn Ser Ala Leu Lys Ala Trp Leu Asp Ser Ser Tyr Leu Ser
1               5                   10                  15 ggc gca aac cag agc tgg ata gaa cag ctc tat gaa gac ttc tta acc     96
Gly Ala Asn Gln Ser Trp Ile Glu Gln Leu Tyr Glu Asp Phe Leu Thr
            20                  25                  30 gat cct gac tcg gtt gac gct aac tgg cgt tcg acg ttc cag cag tta    144
Asp Pro Asp Ser Val Asp Ala Asn Trp Arg Ser Thr Phe Gln Gln Leu
        35                  40                  45 cct ggt acg gga gtc aaa ccg gat caa ttc cac tct caa acg cgt gaa    192
Pro Gly Thr Gly Val Lys Pro Asp Gln Phe His Ser Gln Thr Arg Glu
    50                  55                  60 tat ttc cgc cgc ctg gcg aaa gac gct tca cgt tac tct tca acg atc    240
Tyr Phe Arg Arg Leu Ala Lys Asp Ala Ser Arg Tyr Ser Ser Thr Ile
65                  70                  75                  80 tcc gac cct gac acc aat gtg aag cag gtt aaa gtc ctg cag ctc att    288
Ser Asp Pro Asp Thr Asn Val Lys Gln Val Lys Val Leu Gln Leu Ile
                85                  90                  95 aac gca tac cgc ttc cgt ggt cac cag cat gcg aat ctc gat ccg ctg    336
Asn Ala Tyr Arg Phe Arg Gly His Gln His Ala Asn Leu Asp Pro Leu
            100                 105                 110 gga ctg tgg cag caa gat aaa gtg gcc gat ctg gat ccg tct ttc cac    384
Gly Leu Trp Gln Gln Asp Lys Val Ala Asp Leu Asp Pro Ser Phe His
        115                 120                 125 gat ctg acc gaa gca gac ttc cag gag acc ttc aac gtc ggt tca ttt    432
Asp Leu Thr Glu Ala Asp Phe Gln Glu Thr Phe Asn Val Gly Ser Phe
    130                 135                 140 gcc agc ggc aaa gaa acc atg aaa ctc ggc gag ctg ctg gaa gcc ctc    480
Ala Ser Gly Lys Glu Thr Met Lys Leu Gly Glu Leu Leu Glu Ala Leu
145                 150                 155                 160 aag caa acc tac tgc ggc ccg att ggt gcc gag tat atg cac att acc    528
Lys Gln Thr Tyr Cys Gly Pro Ile Gly Ala Glu Tyr Met His Ile Thr
                165                 170                 175 agc acc gaa gaa aaa cgc tgg atc caa cag cgt atc gag tct ggt cgc    576
Ser Thr Glu Glu Lys Arg Trp Ile Gln Gln Arg Ile Glu Ser Gly Arg
```

```
                180                  185                  190
gcg act ttc aat agc gaa gag aaa aaa cgc ttc tta agc gaa ctg acc       624
Ala Thr Phe Asn Ser Glu Glu Lys Lys Arg Phe Leu Ser Glu Leu Thr
        195                  200                  205 gcc gct gaa ggt ctt gaa cgt tac ctc ggc gca aaa ttc cct ggc gca       672
Ala Ala Glu Gly Leu Glu Arg Tyr Leu Gly Ala Lys Phe Pro Gly Ala
    210                  215                  220 aaa cgc ttc tcg ctg gaa ggc ggt gac gcg tta atc ccg atg ctt aaa       720
Lys Arg Phe Ser Leu Glu Gly Gly Asp Ala Leu Ile Pro Met Leu Lys
225                  230                  235                  240 gag atg atc cgc cac gct ggc aac agc ggc acc cgc gaa gtg gtt ctc       768
Glu Met Ile Arg His Ala Gly Asn Ser Gly Thr Arg Glu Val Val Leu
                245                  250                  255 ggg atg gcg cac cgt ggt cgt ctg aac gtg ctg gtg aac gtg ctg ggt       816
Gly Met Ala His Arg Gly Arg Leu Asn Val Leu Val Asn Val Leu Gly
            260                  265                  270 aaa aaa ccg caa gac ttg ttc gac gag ttc gcc ggt aaa cat aaa gaa       864
Lys Lys Pro Gln Asp Leu Phe Asp Glu Phe Ala Gly Lys His Lys Glu
        275                  280                  285 cac ctc ggc acg ggt gac gtg aaa tac cac atg ggc ttc tcg tct gac       912
His Leu Gly Thr Gly Asp Val Lys Tyr His Met Gly Phe Ser Ser Asp
    290                  295                  300 ttc cag acc gat ggc ggc ctg gtg cac ctg gcg ctg gcg ttt aac ccg       960
Phe Gln Thr Asp Gly Gly Leu Val His Leu Ala Leu Ala Phe Asn Pro
305                  310                  315                  320 tct cac ctt gag att gta agc ccg gta gtt atc ggt tct gtt cgt gcc      1008
Ser His Leu Glu Ile Val Ser Pro Val Val Ile Gly Ser Val Arg Ala
                325                  330                  335 cgt ctg gac aga ctt gat gag ccg agc agc aac aaa gtg ctg cca atc      1056
Arg Leu Asp Arg Leu Asp Glu Pro Ser Ser Asn Lys Val Leu Pro Ile
            340                  345                  350 acc atc cac ggt gac gcc gca gtg acc ggg cag ggc gtg gtt cag gaa      1104
Thr Ile His Gly Asp Ala Ala Val Thr Gly Gln Gly Val Val Gln Glu
        355                  360                  365 acc ctg aac atg tcg aaa gcg cgt ggt tat gaa gtt ggc ggt acg gta      1152
Thr Leu Asn Met Ser Lys Ala Arg Gly Tyr Glu Val Gly Gly Thr Val
    370                  375                  380 cgt atc gtt atc aac aac cag gtt ggt ttc acc acc tct aat ccg ctg      1200
Arg Ile Val Ile Asn Asn Gln Val Gly Phe Thr Thr Ser Asn Pro Leu
385                  390                  395                  400 gat gcc cgt tct acg ccg tac tgt act gat atc ggt aag atg gtt cag      1248
Asp Ala Arg Ser Thr Pro Tyr Cys Thr Asp Ile Gly Lys Met Val Gln
                405                  410                  415 gcc ccg att ttc cac gtt aac gcg gac gat ccg gaa gcc gtt gcc ttt      1296
Ala Pro Ile Phe His Val Asn Ala Asp Asp Pro Glu Ala Val Ala Phe
            420                  425                  430 gtg acc cgt ctg gcg ctc gat ttc cgt aac acc ttt aaa cgt gat gtc      1344
Val Thr Arg Leu Ala Leu Asp Phe Arg Asn Thr Phe Lys Arg Asp Val
        435                  440                  445 ttc atc gac ctg gtg tgc tac cgc cgt cac ggc cac aac gaa gcc gac      1392
Phe Ile Asp Leu Val Cys Tyr Arg Arg His Gly His Asn Glu Ala Asp
    450                  455                  460 gag ccg agc gca acc cag ccg ctg atg tat cag aaa atc aaa aaa cat      1440
Glu Pro Ser Ala Thr Gln Pro Leu Met Tyr Gln Lys Ile Lys Lys His
465                  470                  475                  480 ccg aca ccg cgc aaa atc tac gct gac aag ctg gag cag gaa aaa gtg      1488
Pro Thr Pro Arg Lys Ile Tyr Ala Asp Lys Leu Glu Gln Glu Lys Val
                485                  490                  495 gcg acg ctg gaa gat gcc acc gag atg gtt aac ctg tac cgc gat gcg      1536
Ala Thr Leu Glu Asp Ala Thr Glu Met Val Asn Leu Tyr Arg Asp Ala
```

-continued

```
                    500                 505                 510
ctg gat gct ggc gat tgc gta gtg gca gag tgg cgt ccg atg aac atg          1584
Leu Asp Ala Gly Asp Cys Val Val Ala Glu Trp Arg Pro Met Asn Met
            515                 520                 525 cac tct ttc acc tgg tcg ccg tac ctc aac cac gaa tgg gac gaa gag          1632
His Ser Phe Thr Trp Ser Pro Tyr Leu Asn His Glu Trp Asp Glu Glu
530                 535                 540 tac ccg aac aaa gtt gag atg aag cgc ctg cag gag ctg gcg aaa cgc          1680
Tyr Pro Asn Lys Val Glu Met Lys Arg Leu Gln Glu Leu Ala Lys Arg
545                 550                 555                 560 atc agc acg gtg ccg gaa gca gtt gaa atg cag tct cgc gtt gcc aag          1728
Ile Ser Thr Val Pro Glu Ala Val Glu Met Gln Ser Arg Val Ala Lys
                565                 570                 575 att tat ggc gat cgc cag gcg atg gct gcc ggt gag aaa ctg ttc gac          1776
Ile Tyr Gly Asp Arg Gln Ala Met Ala Ala Gly Glu Lys Leu Phe Asp
            580                 585                 590 tgg ggc ggt gcg gaa aac ctc gct tac gcc acg ctg gtt gat gaa ggc          1824
Trp Gly Gly Ala Glu Asn Leu Ala Tyr Ala Thr Leu Val Asp Glu Gly
        595                 600                 605 att ccg gtt cgc ctg tcg ggt gaa gac tcc ggt cgc ggt acc ttc ttc          1872
Ile Pro Val Arg Leu Ser Gly Glu Asp Ser Gly Arg Gly Thr Phe Phe
610                 615                 620 cac cgc cac gcg gtg atc cac aac cag tct aac ggt tcc act tac acg          1920
His Arg His Ala Val Ile His Asn Gln Ser Asn Gly Ser Thr Tyr Thr
625                 630                 635                 640 ccg ctg caa cat atc cat aac ggg cag ggc gcg ttc cgt gtc tgg gac          1968
Pro Leu Gln His Ile His Asn Gly Gln Gly Ala Phe Arg Val Trp Asp
                645                 650                 655 tcc gta ctg tct gaa gaa gca gtg ctg gcg ttt gaa tat ggt tat gcc          2016
Ser Val Leu Ser Glu Glu Ala Val Leu Ala Phe Glu Tyr Gly Tyr Ala
            660                 665                 670 acc gca gaa cca cgc act ctg acc atc tgg gaa gcg cag ttc ggt gac          2064
Thr Ala Glu Pro Arg Thr Leu Thr Ile Trp Glu Ala Gln Phe Gly Asp
        675                 680                 685 ttc gcc aac ggt gcg cag gtg gtt atc gac cag ttc atc tcc tct ggc          2112
Phe Ala Asn Gly Ala Gln Val Val Ile Asp Gln Phe Ile Ser Ser Gly
690                 695                 700 gaa cag aaa tgg ggc cgg atg tgt ggt ctg gtg atg ttg ctg ccg cac          2160
Glu Gln Lys Trp Gly Arg Met Cys Gly Leu Val Met Leu Leu Pro His
705                 710                 715                 720 ggt tac gaa ggg cag ggg ccg gag cac tcc tcc gcg cgt ctg gaa cgt          2208
Gly Tyr Glu Gly Gln Gly Pro Glu His Ser Ser Ala Arg Leu Glu Arg
                725                 730                 735 tat ctg caa ctt tgt gct gag caa aac atg cag gtt tgc gta ccg tct          2256
Tyr Leu Gln Leu Cys Ala Glu Gln Asn Met Gln Val Cys Val Pro Ser
            740                 745                 750 acc ccg gca cag gtt tac cac atg ctg cgt cgt cag gcg ctg cgc ggg          2304
Thr Pro Ala Gln Val Tyr His Met Leu Arg Arg Gln Ala Leu Arg Gly
        755                 760                 765 atg cgt cgt ccg ctg gtc gtg atg tcg ccg aaa tcc ctg ctg cgt cat          2352
Met Arg Arg Pro Leu Val Val Met Ser Pro Lys Ser Leu Leu Arg His
770                 775                 780 ccg ctg gcg gtt tcc agc ctc gaa gaa ctg gcg aac ggc acc ttc ctg          2400
Pro Leu Ala Val Ser Ser Leu Glu Glu Leu Ala Asn Gly Thr Phe Leu
785                 790                 795                 800 cca gcc atc ggt gaa atc gac gag ctt gat ccg aag ggc gtg aag cgc          2448
Pro Ala Ile Gly Glu Ile Asp Glu Leu Asp Pro Lys Gly Val Lys Arg
                805                 810                 815 gta gtg atg tgt tct ggt aag gtt tat tac gac ctg ctg gaa cag cgt          2496
Val Val Met Cys Ser Gly Lys Val Tyr Tyr Asp Leu Leu Glu Gln Arg
```

```
                        820                 825                 830
cgt aag aac aat caa cac gat gtc gcc att gtg cgt atc gag caa ctc        2544
Arg Lys Asn Asn Gln His Asp Val Ala Ile Val Arg Ile Glu Gln Leu
        835                 840                 845 tac ccg ttc ccg cat aaa gcg atg cag gaa gtg ttg cag cag ttt gct        2592
Tyr Pro Phe Pro His Lys Ala Met Gln Glu Val Leu Gln Gln Phe Ala
850                 855                 860 cac gtc aag gat ttt gtc tgg tgc cag gaa gag ccg ctc aac cag ggc        2640
His Val Lys Asp Phe Val Trp Cys Gln Glu Glu Pro Leu Asn Gln Gly
865                 870                 875                 880 gca tgg tac tgc agc cag cat cat ttc cgt gaa gtg att ccg ttt ggg        2688
Ala Trp Tyr Cys Ser Gln His His Phe Arg Glu Val Ile Pro Phe Gly
            885                 890                 895 gct tct ctg cgt tat gca ggc cgc ccg gcc tcc gcc tct ccg gcg gta        2736
Ala Ser Leu Arg Tyr Ala Gly Arg Pro Ala Ser Ala Ser Pro Ala Val
            900                 905                 910 ggg tat atg tcc gtt cac cag aaa cag caa caa gat ctg gtt aat gac        2784
Gly Tyr Met Ser Val His Gln Lys Gln Gln Gln Asp Leu Val Asn Asp
        915                 920                 925 gcg ctg aac gtc gaa taa                                                2802
Ala Leu Asn Val Glu
    930

<210> SEQ ID NO 6
<211> LENGTH: 933
<212> TYPE: PRT
<213> ORGANISM: Escherichia coli

<400> SEQUENCE: 6

Met Gln Asn Ser Ala Leu Lys Ala Trp Leu Asp Ser Ser Tyr Leu Ser
1               5                   10                  15

Gly Ala Asn Gln Ser Trp Ile Glu Gln Leu Tyr Glu Asp Phe Leu Thr
            20                  25                  30

Asp Pro Asp Ser Val Asp Ala Asn Trp Arg Ser Thr Phe Gln Gln Leu
        35                  40                  45

Pro Gly Thr Gly Val Lys Pro Asp Gln Phe His Ser Gln Thr Arg Glu
    50                  55                  60

Tyr Phe Arg Arg Leu Ala Lys Asp Ala Ser Arg Tyr Ser Ser Thr Ile
65                  70                  75                  80

Ser Asp Pro Asp Thr Asn Val Lys Gln Val Lys Val Leu Gln Leu Ile
                85                  90                  95

Asn Ala Tyr Arg Phe Arg Gly His Gln His Ala Asn Leu Asp Pro Leu
            100                 105                 110

Gly Leu Trp Gln Gln Asp Lys Val Ala Asp Leu Asp Pro Ser Phe His
        115                 120                 125

Asp Leu Thr Glu Ala Asp Phe Gln Glu Thr Phe Asn Val Gly Ser Phe
    130                 135                 140

Ala Ser Gly Lys Glu Thr Met Lys Leu Gly Glu Leu Leu Glu Ala Leu
145                 150                 155                 160

Lys Gln Thr Tyr Cys Gly Pro Ile Gly Ala Glu Tyr Met His Ile Thr
                165                 170                 175

Ser Thr Glu Glu Lys Arg Trp Ile Gln Gln Arg Ile Glu Ser Gly Arg
            180                 185                 190

Ala Thr Phe Asn Ser Glu Glu Lys Arg Phe Leu Ser Glu Leu Thr
        195                 200                 205

Ala Ala Glu Gly Leu Glu Arg Tyr Leu Gly Ala Lys Phe Pro Gly Ala
    210                 215                 220
```

-continued

```
Lys Arg Phe Ser Leu Glu Gly Gly Asp Ala Leu Ile Pro Met Leu Lys
225                 230                 235                 240

Glu Met Ile Arg His Ala Gly Asn Ser Thr Arg Glu Val Val Leu
            245                 250                 255

Gly Met Ala His Arg Gly Arg Leu Asn Val Leu Val Asn Val Leu Gly
                260                 265                 270

Lys Lys Pro Gln Asp Leu Phe Asp Glu Phe Ala Gly Lys His Lys Glu
            275                 280                 285

His Leu Gly Thr Gly Asp Val Lys Tyr His Met Gly Phe Ser Ser Asp
        290                 295                 300

Phe Gln Thr Asp Gly Gly Leu Val His Leu Ala Leu Ala Phe Asn Pro
305                 310                 315                 320

Ser His Leu Glu Ile Val Ser Pro Val Val Ile Gly Ser Val Arg Ala
                325                 330                 335

Arg Leu Asp Arg Leu Asp Glu Pro Ser Ser Asn Lys Val Leu Pro Ile
            340                 345                 350

Thr Ile His Gly Asp Ala Ala Val Thr Gly Gln Gly Val Val Gln Glu
        355                 360                 365

Thr Leu Asn Met Ser Lys Ala Arg Gly Tyr Glu Val Gly Gly Thr Val
370                 375                 380

Arg Ile Val Ile Asn Asn Gln Val Gly Phe Thr Thr Ser Asn Pro Leu
385                 390                 395                 400

Asp Ala Arg Ser Thr Pro Tyr Cys Thr Asp Ile Gly Lys Met Val Gln
                405                 410                 415

Ala Pro Ile Phe His Val Asn Ala Asp Asp Pro Glu Ala Val Ala Phe
            420                 425                 430

Val Thr Arg Leu Ala Leu Asp Phe Arg Asn Thr Phe Lys Arg Asp Val
        435                 440                 445

Phe Ile Asp Leu Val Cys Tyr Arg Arg His Gly His Asn Glu Ala Asp
450                 455                 460

Glu Pro Ser Ala Thr Gln Pro Leu Met Tyr Gln Lys Ile Lys Lys His
465                 470                 475                 480

Pro Thr Pro Arg Lys Ile Tyr Ala Asp Lys Leu Glu Gln Glu Lys Val
                485                 490                 495

Ala Thr Leu Glu Asp Ala Thr Glu Met Val Asn Leu Tyr Arg Asp Ala
            500                 505                 510

Leu Asp Ala Gly Asp Cys Val Val Ala Glu Trp Arg Pro Met Asn Met
        515                 520                 525

His Ser Phe Thr Trp Ser Pro Tyr Leu Asn His Glu Trp Asp Glu Glu
530                 535                 540

Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
                565                 570                 575

Ile Tyr Gly Asp Arg Gln Ala Met Ala Ala Gly Glu Lys Leu Phe Asp
            580                 585                 590

Trp Gly Gly Ala Glu Asn Leu Ala Tyr Ala Thr Leu Val Asp Glu Gly
        595                 600                 605

Ile Pro Val Arg Leu Ser Gly Glu Asp Ser Arg Gly Thr Phe Phe
610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655
```

```
Ser Val Leu Ser Glu Glu Ala Val Leu Ala Phe Glu Tyr Gly Tyr Ala
            660                 665                 670

Thr Ala Glu Pro Arg Thr Leu Thr Ile Trp Glu Ala Gln Phe Gly Asp
        675                 680                 685

Phe Ala Asn Gly Ala Gln Val Val Ile Asp Gln Phe Ile Ser Ser Gly
    690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
            740                 745                 750

Thr Pro Ala Gln Val Tyr His Met Leu Arg Arg Gln Ala Leu Arg Gly
        755                 760                 765

Met Arg Arg Pro Leu Val Val Met Ser Pro Lys Ser Leu Leu Arg His
    770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
            820                 825                 830

Arg Lys Asn Asn Gln His Asp Val Ala Ile Val Arg Ile Glu Gln Leu
        835                 840                 845

Tyr Pro Phe Pro His Lys Ala Met Gln Glu Val Leu Gln Gln Phe Ala
    850                 855                 860

His Val Lys Asp Phe Val Trp Cys Gln Glu Glu Pro Leu Asn Gln Gly
865                 870                 875                 880

Ala Trp Tyr Cys Ser Gln His His Phe Arg Glu Val Ile Pro Phe Gly
                885                 890                 895

Ala Ser Leu Arg Tyr Ala Gly Arg Pro Ala Ser Ala Ser Pro Ala Val
            900                 905                 910

Gly Tyr Met Ser Val His Gln Lys Gln Gln Gln Asp Leu Val Asn Asp
        915                 920                 925

Ala Leu Asn Val Glu
        930

<210> SEQ ID NO 7
<211> LENGTH: 1218
<212> TYPE: DNA
<213> ORGANISM: Escherichia coli
<220> FEATURE:
<221> NAME/KEY: CDS
<222> LOCATION: (1)..(1218)

<400> SEQUENCE: 7 atg agt agc gta gat att ctg gtc cct gac ctg cct gaa tcc gta gcc      48
Met Ser Ser Val Asp Ile Leu Val Pro Asp Leu Pro Glu Ser Val Ala
1               5                   10                  15 gat gcc acc gtc gca acc tgg cat aaa aaa ccc ggc gac gca gtc gta      96
Asp Ala Thr Val Ala Thr Trp His Lys Lys Pro Gly Asp Ala Val Val
            20                  25                  30 cgt gat gaa gtg ctg gta gaa atc gaa act gac aaa gtg gta ctg gaa     144
Arg Asp Glu Val Leu Val Glu Ile Glu Thr Asp Lys Val Val Leu Glu
        35                  40                  45 gta ccg gca tca gca gac ggc att ctg gat gcg gtt ctg gaa gat gaa     192
Val Pro Ala Ser Ala Asp Gly Ile Leu Asp Ala Val Leu Glu Asp Glu
```

```
                50                     55                      60
ggt aca acg gta acg tct cgt cag atc ctt ggt cgc ctg cgt gaa ggc       240
Gly Thr Thr Val Thr Ser Arg Gln Ile Leu Gly Arg Leu Arg Glu Gly
 65                      70                      75                  80 aac agc gcc ggt aaa gaa acc agc gcc aaa tct gaa gag aaa gcg tcc       288
Asn Ser Ala Gly Lys Glu Thr Ser Ala Lys Ser Glu Glu Lys Ala Ser
                     85                      90                      95 act ccg gcg caa cgc cag cag gcg tct ctg gaa gag caa aac aac gat       336
Thr Pro Ala Gln Arg Gln Gln Ala Ser Leu Glu Glu Gln Asn Asn Asp
                100                     105                     110 gcg tta agc ccg gcg atc cgt cgc ctg ctg gct gaa cac aat ctc gac       384
Ala Leu Ser Pro Ala Ile Arg Arg Leu Leu Ala Glu His Asn Leu Asp
            115                     120                     125 gcc agc gcc att aaa ggc acc ggt gtg ggt ggt cgt ctg act cgt gaa       432
Ala Ser Ala Ile Lys Gly Thr Gly Val Gly Gly Arg Leu Thr Arg Glu
        130                     135                     140 gat gtg gaa aaa cat ctg gcg aaa gcc ccg gcg aaa gag tct gct ccg       480
Asp Val Glu Lys His Leu Ala Lys Ala Pro Ala Lys Glu Ser Ala Pro
145                     150                     155                 160 gca gcg gct gct ccg gcg gcg caa ccg gct ctg gct gca cgt agt gaa       528
Ala Ala Ala Ala Pro Ala Ala Gln Pro Ala Leu Ala Ala Arg Ser Glu
                    165                     170                     175 aaa cgt gtc ccg atg act cgc ctg cgt aag cgt gtg gca gag cgt ctg       576
Lys Arg Val Pro Met Thr Arg Leu Arg Lys Arg Val Ala Glu Arg Leu
                180                     185                     190 ctg gaa gcg aaa aac tcc acc gcc atg ctg acc acg ttc aac gaa gtc       624
Leu Glu Ala Lys Asn Ser Thr Ala Met Leu Thr Thr Phe Asn Glu Val
            195                     200                     205 aac atg aag ccg att atg gat ctg cgt aag cag tac ggt gaa gcg ttt       672
Asn Met Lys Pro Ile Met Asp Leu Arg Lys Gln Tyr Gly Glu Ala Phe
        210                     215                     220 gaa aaa cgc cac ggc atc cgt ctg ggc ttt atg tcc ttc tac gtg aaa       720
Glu Lys Arg His Gly Ile Arg Leu Gly Phe Met Ser Phe Tyr Val Lys
225                     230                     235                 240 gcg gtg gtt gaa gcc ctg aaa cgt tac ccg gaa gtg aac gct tct atc       768
Ala Val Val Glu Ala Leu Lys Arg Tyr Pro Glu Val Asn Ala Ser Ile
                    245                     250                     255 gac ggc gat gac gtg gtt tac cac aac tat ttc gac gtc agc atg gcg       816
Asp Gly Asp Asp Val Val Tyr His Asn Tyr Phe Asp Val Ser Met Ala
                260                     265                     270 gtt tct acg ccg cgc ggc ctg gtg acg ccg gtt ctg cgt gat gtc gat       864
Val Ser Thr Pro Arg Gly Leu Val Thr Pro Val Leu Arg Asp Val Asp
            275                     280                     285 acc ctc ggc atg gca gac atc gag aag aaa atc aaa gag ctg gca gtc       912
Thr Leu Gly Met Ala Asp Ile Glu Lys Lys Ile Lys Glu Leu Ala Val
        290                     295                     300 aaa ggc cgt gac ggc aag ctg acc gtt gaa gat ctg acc ggt ggt aac       960
Lys Gly Arg Asp Gly Lys Leu Thr Val Glu Asp Leu Thr Gly Gly Asn
305                     310                     315                 320 ttc acc atc acc aac ggt ggt gtg ttc ggt tcc ctg atg tct acg ccg      1008
Phe Thr Ile Thr Asn Gly Gly Val Phe Gly Ser Leu Met Ser Thr Pro
                    325                     330                     335 atc atc aac ccg ccg cag agc gca att ctg ggt atg cac gct atc aaa      1056
Ile Ile Asn Pro Pro Gln Ser Ala Ile Leu Gly Met His Ala Ile Lys
                340                     345                     350 gat cgt ccg atg gcg gtg aat ggt cag gtt gag atc ctg ccg atg atg      1104
Asp Arg Pro Met Ala Val Asn Gly Gln Val Glu Ile Leu Pro Met Met
            355                     360                     365 tac ctg gcg ctg tcc tac gat cac cgt ctg atc gat ggt cgc gaa tcc      1152
Tyr Leu Ala Leu Ser Tyr Asp His Arg Leu Ile Asp Gly Arg Glu Ser
```

```
           370            375             380
gtg ggc ttc ctg gta acg atc aaa gag ttg ctg gaa gat ccg acg cgt      1200
Val Gly Phe Leu Val Thr Ile Lys Glu Leu Leu Glu Asp Pro Thr Arg
385                 390                 395                 400 ctg ctg ctg gac gtg tag                                              1218
Leu Leu Leu Asp Val
                405

<210> SEQ ID NO 8
<211> LENGTH: 405
<212> TYPE: PRT
<213> ORGANISM: Escherichia coli

<400> SEQUENCE: 8

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Val
            20                  25                  30

Arg Asp Glu Val Leu Val Glu Ile Glu Thr Asp Lys Val Val Leu Glu
        35                  40                  45

Val Pro Ala Ser Ala Asp Gly Ile Leu Asp Ala Val Leu Glu Asp Glu
    50                  55                  60

Gly Thr Thr Val Thr Ser Arg Gln Ile Leu Gly Arg Leu Arg Glu Gly
65                  70                  75                  80

Asn Ser Ala Gly Lys Glu Thr Ser Ala Lys Ser Glu Lys Ala Ser
                85                  90                  95

Thr Pro Ala Gln Arg Gln Gln Ala Ser Leu Glu Glu Asn Asn Asp
            100                 105                 110

Ala Leu Ser Pro Ala Ile Arg Arg Leu Leu Ala Glu His Asn Leu Asp
        115                 120                 125

Ala Ser Ala Ile Lys Gly Thr Gly Val Gly Gly Arg Leu Thr Arg Glu
130                 135                 140

Asp Val Glu Lys His Leu Ala Lys Ala Pro Ala Lys Glu Ser Ala Pro
145                 150                 155                 160

Ala Ala Ala Ala Pro Ala Ala Gln Pro Ala Leu Ala Ala Arg Ser Glu
                165                 170                 175

Lys Arg Val Pro Met Thr Arg Leu Arg Lys Arg Val Ala Glu Arg Leu
            180                 185                 190

Leu Glu Ala Lys Asn Ser Thr Ala Met Leu Thr Thr Phe Asn Glu Val
        195                 200                 205

Asn Met Lys Pro Ile Met Asp Leu Arg Lys Gln Tyr Gly Glu Ala Phe
    210                 215                 220

Glu Lys Arg His Gly Ile Arg Leu Gly Phe Met Ser Phe Tyr Val Lys
225                 230                 235                 240

Ala Val Val Glu Ala Leu Lys Arg Tyr Pro Glu Val Asn Ala Ser Ile
                245                 250                 255

Asp Gly Asp Asp Val Val Tyr His Asn Tyr Phe Asp Val Ser Met Ala
            260                 265                 270

Val Ser Thr Pro Arg Gly Leu Val Thr Pro Val Leu Arg Asp Val Asp
        275                 280                 285

Thr Leu Gly Met Ala Asp Ile Glu Lys Lys Ile Lys Glu Leu Ala Val
    290                 295                 300

Lys Gly Arg Asp Gly Lys Leu Thr Val Glu Asp Leu Thr Gly Gly Asn
305                 310                 315                 320

Phe Thr Ile Thr Asn Gly Gly Val Phe Gly Ser Leu Met Ser Thr Pro
                325                 330                 335
```

```
Ile Ile Asn Pro Pro Gln Ser Ala Ile Leu Gly Met His Ala Ile Lys
            340                 345                 350

Asp Arg Pro Met Ala Val Asn Gly Gln Val Glu Ile Leu Pro Met Met
            355                 360                 365

Tyr Leu Ala Leu Ser Tyr Asp His Arg Leu Ile Asp Gly Arg Glu Ser
            370                 375                 380

Val Gly Phe Leu Val Thr Ile Lys Glu Leu Leu Glu Asp Pro Thr Arg
385                 390                 395                 400

Leu Leu Leu Asp Val
            405

<210> SEQ ID NO 9
<211> LENGTH: 1305
<212> TYPE: DNA
<213> ORGANISM: Escherichia coli
<220> FEATURE:
<221> NAME/KEY: CDS
<222> LOCATION: (1)..(1305)

<400> SEQUENCE: 9 atg aaa acc cgt aca caa caa att gaa gaa tta cag aaa gag tgg act      48
Met Lys Thr Arg Thr Gln Gln Ile Glu Glu Leu Gln Lys Glu Trp Thr
1               5                   10                  15 caa ccg cgt tgg gaa ggc att act cgc cca tac agt gcg gaa gat gtg     96
Gln Pro Arg Trp Glu Gly Ile Thr Arg Pro Tyr Ser Ala Glu Asp Val
            20                  25                  30 gtg aaa tta cgc ggt tca gtc aat cct gaa tgc acg ctg gcg caa ctg    144
Val Lys Leu Arg Gly Ser Val Asn Pro Glu Cys Thr Leu Ala Gln Leu
        35                  40                  45 ggc gca gcg aaa atg tgg cgt ctg ctg cac ggt gag tcg aaa aaa ggc    192
Gly Ala Ala Lys Met Trp Arg Leu Leu His Gly Glu Ser Lys Lys Gly
    50                  55                  60 tac atc aac agc ctc ggc gca ctg act ggc ggt cag gcg ctg caa cag    240
Tyr Ile Asn Ser Leu Gly Ala Leu Thr Gly Gly Gln Ala Leu Gln Gln
65                  70                  75                  80 gcg aaa gcg ggt att gaa gca gtc tat ctg tcg gga tgg cag gta gcg    288
Ala Lys Ala Gly Ile Glu Ala Val Tyr Leu Ser Gly Trp Gln Val Ala
            85                  90                  95 gcg gac gct aac ctg gcg gcc agc atg tat ccg gat cag tcg ctc tat    336
Ala Asp Ala Asn Leu Ala Ala Ser Met Tyr Pro Asp Gln Ser Leu Tyr
            100                 105                 110 ccg gca aac tcg gtg cca gct gtg gtg gag cgg atc aac aac acc ttc    384
Pro Ala Asn Ser Val Pro Ala Val Val Glu Arg Ile Asn Asn Thr Phe
        115                 120                 125 cgt cgt gcc gat cag atc caa tgg tcc gcg ggc att gag ccg ggc gat    432
Arg Arg Ala Asp Gln Ile Gln Trp Ser Ala Gly Ile Glu Pro Gly Asp
    130                 135                 140 ccg cgc tat gtc gat tac ttc ctg ccg atc gtt gcc gat gcg gaa gcc    480
Pro Arg Tyr Val Asp Tyr Phe Leu Pro Ile Val Ala Asp Ala Glu Ala
145                 150                 155                 160 ggt ttt ggc ggt gtc ctg aat gcc ttt gaa ctg atg aaa gcg atg att    528
Gly Phe Gly Gly Val Leu Asn Ala Phe Glu Leu Met Lys Ala Met Ile
            165                 170                 175 gaa gcc ggt gca gcg gca gtt cac ttc gaa gat cag ctg gcg tca gtg    576
Glu Ala Gly Ala Ala Ala Val His Phe Glu Asp Gln Leu Ala Ser Val
            180                 185                 190 aag aaa tgc ggt cac atg ggc ggc aaa gtt tta gtg cca act cag gaa    624
Lys Lys Cys Gly His Met Gly Gly Lys Val Leu Val Pro Thr Gln Glu
        195                 200                 205 gct att cag aaa ctg gtc gcg gcg cgt ctg gca gct gac gtg acg ggc    672
```

```
            Ala Ile Gln Lys Leu Val Ala Ala Arg Leu Ala Ala Asp Val Thr Gly
                210             215                 220 gtt cca acc ctg ctg gtt gcc cgt acc gat gct gat gcg gcg gat ctg         720
Val Pro Thr Leu Leu Val Ala Arg Thr Asp Ala Asp Ala Ala Asp Leu
225                 230                 235                 240 atc acc tcc gat tgc gac ccg tat gac agc gaa ttt att acc ggc gag         768
Ile Thr Ser Asp Cys Asp Pro Tyr Asp Ser Glu Phe Ile Thr Gly Glu
                245                 250                 255 cgt acc agt gaa ggc ttc ttc cgt act cat gcg ggc att gag caa gcg         816
Arg Thr Ser Glu Gly Phe Phe Arg Thr His Ala Gly Ile Glu Gln Ala
            260                 265                 270 atc agc cgt ggc ctg gcg tat gcg cca tat gct gac ctg gtc tgg tgt         864
Ile Ser Arg Gly Leu Ala Tyr Ala Pro Tyr Ala Asp Leu Val Trp Cys
        275                 280                 285 gaa acc tcc acg ccg gat ctg gaa ctg gcg cgt cgc ttt gca caa gct         912
Glu Thr Ser Thr Pro Asp Leu Glu Leu Ala Arg Arg Phe Ala Gln Ala
    290                 295                 300 atc cac gcg aaa tat ccg ggc aaa ctg ctg gct tat aac tgc tcg ccg         960
Ile His Ala Lys Tyr Pro Gly Lys Leu Leu Ala Tyr Asn Cys Ser Pro
305                 310                 315                 320 tcg ttc aac tgg cag aaa aac ctc gac gac aaa act att gcc agc ttc        1008
Ser Phe Asn Trp Gln Lys Asn Leu Asp Asp Lys Thr Ile Ala Ser Phe
                325                 330                 335 cag cag cag ctg tcg gat atg ggc tac aag ttc cag ttc atc acc ctg        1056
Gln Gln Gln Leu Ser Asp Met Gly Tyr Lys Phe Gln Phe Ile Thr Leu
                340                 345                 350 gca ggt atc cac agc atg tgg ttc aac atg ttt gac ctg gca aac gcc        1104
Ala Gly Ile His Ser Met Trp Phe Asn Met Phe Asp Leu Ala Asn Ala
            355                 360                 365 tat gcc cag ggc gag ggt atg aag cac tac gtt gag aaa gtg cag cag        1152
Tyr Ala Gln Gly Glu Gly Met Lys His Tyr Val Glu Lys Val Gln Gln
        370                 375                 380 ccg gaa ttt gcc gcc gcg aaa gat ggc tat acc ttc gta tct cac cag        1200
Pro Glu Phe Ala Ala Ala Lys Asp Gly Tyr Thr Phe Val Ser His Gln
385                 390                 395                 400 cag gaa gtg ggt aca ggt tac ttc gat aaa gtg acg act att att cag        1248
Gln Glu Val Gly Thr Gly Tyr Phe Asp Lys Val Thr Thr Ile Ile Gln
                405                 410                 415 ggc ggc acg tct tca gtc acc gcg ctg acc ggc tcc act gaa gaa tcg        1296
Gly Gly Thr Ser Ser Val Thr Ala Leu Thr Gly Ser Thr Glu Glu Ser
                420                 425                 430 cag ttc taa                                                             1305
Gln Phe <210> SEQ ID NO 10
<211> LENGTH: 434
<212> TYPE: PRT
<213> ORGANISM: Escherichia coli

<400> SEQUENCE: 10

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80
```

```
Ala Lys Ala Gly Ile Glu Ala Val Tyr Leu Ser Gly Trp Gln Val Ala
                 85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
            115                 120                 125

Arg Arg Ala Asp Gln Ile Gln Trp Ser Ala Gly Ile Glu Pro Gly Asp
        130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Val His Phe Glu Asp Gln Leu Ala Ser Val
            180                 185                 190

Lys Lys Cys Gly His Met Gly Gly Lys Val Leu Val Pro Thr Gln Glu
            195                 200                 205

Ala Ile Gln Lys Leu Val Ala Ala Arg Leu Ala Ala Asp Val Thr Gly
        210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe

<210> SEQ ID NO 11
<211> LENGTH: 1602
<212> TYPE: DNA
<213> ORGANISM: Escherichia coli
<220> FEATURE:
<221> NAME/KEY: CDS
<222> LOCATION: (1)..(1602)

<400> SEQUENCE: 11
```

```
atg act gaa cag gca aca aca acc gat gaa ctg gct ttc aca agg ccg      48
Met Thr Glu Gln Ala Thr Thr Thr Asp Glu Leu Ala Phe Thr Arg Pro
1               5                   10                  15 tat ggc gag cag gag aag caa att ctt act gcc gaa gcg gta gaa ttt      96
Tyr Gly Glu Gln Glu Lys Gln Ile Leu Thr Ala Glu Ala Val Glu Phe
                20                  25                  30 ctg act gag ctg gtg acg cat ttt acg cca caa cgc aat aaa ctt ctg     144
Leu Thr Glu Leu Val Thr His Phe Thr Pro Gln Arg Asn Lys Leu Leu
            35                  40                  45 gca gcg cgc att cag cag cag caa gat att gat aac gga acg ttg cct     192
Ala Ala Arg Ile Gln Gln Gln Gln Asp Ile Asp Asn Gly Thr Leu Pro
        50                  55                  60 gat ttt att tcg gaa aca gct tcc att cgc gat gct gat tgg aaa att     240
Asp Phe Ile Ser Glu Thr Ala Ser Ile Arg Asp Ala Asp Trp Lys Ile
65                  70                  75                  80 cgc ggg att cct gcg gac tta gaa gac cgc cgc gta gag ata act ggc     288
Arg Gly Ile Pro Ala Asp Leu Glu Asp Arg Arg Val Glu Ile Thr Gly
                85                  90                  95 ccg gta gag cgc aag atg gtg atc aac gcg ctc aac gcc aat gtg aaa     336
Pro Val Glu Arg Lys Met Val Ile Asn Ala Leu Asn Ala Asn Val Lys
            100                 105                 110 gtc ttt atg gcc gat ttc gaa gat tca ctg gca cca gac tgg aac aaa     384
Val Phe Met Ala Asp Phe Glu Asp Ser Leu Ala Pro Asp Trp Asn Lys
        115                 120                 125 gtg atc gac ggg caa att aac ctg cgt gat gcg gtt aac ggc acc atc     432
Val Ile Asp Gly Gln Ile Asn Leu Arg Asp Ala Val Asn Gly Thr Ile
130                 135                 140 agt tac acc aat gaa gca ggc aaa att tac cag ctc aag ccc aat cca     480
Ser Tyr Thr Asn Glu Ala Gly Lys Ile Tyr Gln Leu Lys Pro Asn Pro
145                 150                 155                 160 gcg gtt ttg att tgt cgg gta cgc ggt ctg cac ttg ccg gaa aaa cat     528
Ala Val Leu Ile Cys Arg Val Arg Gly Leu His Leu Pro Glu Lys His
                165                 170                 175 gtc acc tgg cgt ggt gag gca atc ccc ggc agc ctg ttt gat ttt gcg     576
Val Thr Trp Arg Gly Glu Ala Ile Pro Gly Ser Leu Phe Asp Phe Ala
            180                 185                 190 ctc tat ttc ttc cac aac tat cag gca ctg ttg gca aag ggc agt ggt     624
Leu Tyr Phe Phe His Asn Tyr Gln Ala Leu Leu Ala Lys Gly Ser Gly
        195                 200                 205 ccc tat ttc tat ctg ccg aaa acc cag tcc tgg cag gaa gcg gcc tgg     672
Pro Tyr Phe Tyr Leu Pro Lys Thr Gln Ser Trp Gln Glu Ala Ala Trp
210                 215                 220 tgg agc gaa gtc ttc agc tat gca gaa gat cgc ttt aat ctg ccg cgc     720
Trp Ser Glu Val Phe Ser Tyr Ala Glu Asp Arg Phe Asn Leu Pro Arg
225                 230                 235                 240 ggc acc atc aag gcg acg ttg ctg att gaa acg ctg ccc gcc gtg ttc     768
Gly Thr Ile Lys Ala Thr Leu Leu Ile Glu Thr Leu Pro Ala Val Phe
                245                 250                 255 cag atg gat gaa atc ctt cac gcg ctg cgt gac cat att gtt ggt ctg     816
Gln Met Asp Glu Ile Leu His Ala Leu Arg Asp His Ile Val Gly Leu
            260                 265                 270 aac tgc ggt cgt tgg gat tac atc ttc agc tat atc aaa acg ttg aaa     864
Asn Cys Gly Arg Trp Asp Tyr Ile Phe Ser Tyr Ile Lys Thr Leu Lys
        275                 280                 285 aac tat ccc gat cgc gtc ctg cca gac aga cag gca gtg acg atg gat     912
Asn Tyr Pro Asp Arg Val Leu Pro Asp Arg Gln Ala Val Thr Met Asp
290                 295                 300 aaa cca ttc ctg aat gct tac tca cgc ctg ttg att aaa acc tgc cat     960
Lys Pro Phe Leu Asn Ala Tyr Ser Arg Leu Leu Ile Lys Thr Cys His
305                 310                 315                 320
```

```
aaa cgc ggt gct ttt gcg atg ggc ggc atg gcg gcg ttt att ccg agc    1008
Lys Arg Gly Ala Phe Ala Met Gly Gly Met Ala Ala Phe Ile Pro Ser
            325                 330                 335 aaa gat gaa gag cac aat aac cag gtg ctc aac aaa gta aaa gcg gat    1056
Lys Asp Glu Glu His Asn Asn Gln Val Leu Asn Lys Val Lys Ala Asp
        340                 345                 350 aaa tcg ctg gaa gcc aat aac ggt cac gat ggc aca tgg atc gct cac    1104
Lys Ser Leu Glu Ala Asn Asn Gly His Asp Gly Thr Trp Ile Ala His
    355                 360                 365 cca ggc ctt gcg gac acg gca atg gcg gta ttc aac gac att ctc ggc    1152
Pro Gly Leu Ala Asp Thr Ala Met Ala Val Phe Asn Asp Ile Leu Gly
370                 375                 380 tcc cgt aaa aat cag ctt gaa gtg atg cgc gaa caa gac gcg ccg att    1200
Ser Arg Lys Asn Gln Leu Glu Val Met Arg Glu Gln Asp Ala Pro Ile
385                 390                 395                 400 act gcc gat cag ctg ctg gca cct tgt gat ggt gaa cgc acc gaa gaa    1248
Thr Ala Asp Gln Leu Leu Ala Pro Cys Asp Gly Glu Arg Thr Glu Glu
            405                 410                 415 ggt atg cgc gcc aac att cgc gtg gct gtg cag tac atc gaa gcg tgg    1296
Gly Met Arg Ala Asn Ile Arg Val Ala Val Gln Tyr Ile Glu Ala Trp
        420                 425                 430 atc tct ggc aac ggc tgt gtg ccg att tat ggc ctg atg gaa gat gcg    1344
Ile Ser Gly Asn Gly Cys Val Pro Ile Tyr Gly Leu Met Glu Asp Ala
    435                 440                 445 gcg acg gct gaa att tcc cgt acc tcg atc tgg cag tgg atc cat cat    1392
Ala Thr Ala Glu Ile Ser Arg Thr Ser Ile Trp Gln Trp Ile His His
450                 455                 460 caa aaa acg ttg agc aat ggc aaa ccg gtg acc aaa gcc ttg ttc cgc    1440
Gln Lys Thr Leu Ser Asn Gly Lys Pro Val Thr Lys Ala Leu Phe Arg
465                 470                 475                 480 cag atg ctg ggc gaa gag atg aaa gtc att gcc agc gaa ctg ggc gaa    1488
Gln Met Leu Gly Glu Glu Met Lys Val Ile Ala Ser Glu Leu Gly Glu
            485                 490                 495 gaa cgt ttc tcc cag ggg cgt ttt gac gat gcc gca cgc ttg atg gaa    1536
Glu Arg Phe Ser Gln Gly Arg Phe Asp Asp Ala Ala Arg Leu Met Glu
        500                 505                 510 cag atc acc act tcc gat gag tta att gat ttc ctg acc ctg cca ggc    1584
Gln Ile Thr Thr Ser Asp Glu Leu Ile Asp Phe Leu Thr Leu Pro Gly
    515                 520                 525 tac cgc ctg tta gcg taa                                            1602
Tyr Arg Leu Leu Ala
        530

<210> SEQ ID NO 12
<211> LENGTH: 533
<212> TYPE: PRT
<213> ORGANISM: Escherichia coli

<400> SEQUENCE: 12

Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu
        35                  40                  45

Ala Ala Arg Ile Gln Gln Gln Asp Ile Asp Asn Gly Thr Leu Pro
    50                  55                  60

Asp Phe Ile Ser Glu Thr Ala Ser Ile Arg Asp Ala Asp Trp Lys Ile
65                  70                  75                  80

Arg Gly Ile Pro Ala Asp Leu Glu Asp Arg Arg Val Glu Ile Thr Gly
```

-continued

```
                85                  90                  95
Pro Val Glu Arg Lys Met Val Ile Asn Ala Leu Asn Ala Asn Val Lys
            100                 105                 110
Val Phe Met Ala Asp Phe Glu Asp Ser Leu Ala Pro Asp Trp Asn Lys
            115                 120                 125
Val Ile Asp Gly Gln Ile Asn Leu Arg Asp Ala Val Asn Gly Thr Ile
            130                 135                 140
Ser Tyr Thr Asn Glu Ala Gly Lys Ile Tyr Gln Leu Lys Pro Asn Pro
145                 150                 155                 160
Ala Val Leu Ile Cys Arg Val Arg Gly Leu His Leu Pro Glu Lys His
                165                 170                 175
Val Thr Trp Arg Gly Glu Ala Ile Pro Gly Ser Leu Phe Asp Phe Ala
            180                 185                 190
Leu Tyr Phe Phe His Asn Tyr Gln Ala Leu Leu Ala Lys Gly Ser Gly
            195                 200                 205
Pro Tyr Phe Tyr Leu Pro Lys Thr Gln Ser Trp Gln Glu Ala Ala Trp
            210                 215                 220
Trp Ser Glu Val Phe Ser Tyr Ala Glu Asp Arg Phe Asn Leu Pro Arg
225                 230                 235                 240
Gly Thr Ile Lys Ala Thr Leu Leu Ile Glu Thr Leu Pro Ala Val Phe
                245                 250                 255
Gln Met Asp Glu Ile Leu His Ala Leu Arg Asp His Ile Val Gly Leu
            260                 265                 270
Asn Cys Gly Arg Trp Asp Tyr Ile Phe Ser Tyr Ile Lys Thr Leu Lys
            275                 280                 285
Asn Tyr Pro Asp Arg Val Leu Pro Asp Arg Gln Ala Val Thr Met Asp
            290                 295                 300
Lys Pro Phe Leu Asn Ala Tyr Ser Arg Leu Leu Ile Lys Thr Cys His
305                 310                 315                 320
Lys Arg Gly Ala Phe Ala Met Gly Gly Met Ala Ala Phe Ile Pro Ser
                325                 330                 335
Lys Asp Glu Glu His Asn Asn Gln Val Leu Asn Lys Val Lys Ala Asp
            340                 345                 350
Lys Ser Leu Glu Ala Asn Asn Gly His Asp Gly Thr Trp Ile Ala His
            355                 360                 365
Pro Gly Leu Ala Asp Thr Ala Met Ala Val Phe Asn Asp Ile Leu Gly
            370                 375                 380
Ser Arg Lys Asn Gln Leu Glu Val Met Arg Glu Gln Asp Ala Pro Ile
385                 390                 395                 400
Thr Ala Asp Gln Leu Leu Ala Pro Cys Asp Gly Glu Arg Thr Glu Glu
                405                 410                 415
Gly Met Arg Ala Asn Ile Arg Val Ala Val Gln Tyr Ile Glu Ala Trp
            420                 425                 430
Ile Ser Gly Asn Gly Cys Val Pro Ile Tyr Gly Leu Met Glu Asp Ala
            435                 440                 445
Ala Thr Ala Glu Ile Ser Arg Thr Ser Ile Trp Gln Trp Ile His His
            450                 455                 460
Gln Lys Thr Leu Ser Asn Gly Lys Pro Val Thr Lys Ala Leu Phe Arg
465                 470                 475                 480
Gln Met Leu Gly Glu Glu Met Lys Val Ile Ala Ser Glu Leu Gly Glu
                485                 490                 495
Glu Arg Phe Ser Gln Gly Arg Phe Asp Asp Ala Ala Arg Leu Met Glu
            500                 505                 510
```

```
Gln Ile Thr Thr Ser Asp Glu Leu Ile Asp Phe Leu Thr Leu Pro Gly
        515                 520                 525

Tyr Arg Leu Leu Ala
        530

<210> SEQ ID NO 13
<211> LENGTH: 930
<212> TYPE: DNA
<213> ORGANISM: Escherichia coli
<220> FEATURE:
<221> NAME/KEY: CDS
<222> LOCATION: (1)..(930)

<400> SEQUENCE: 13 atg acc acg aag aaa gct gat tac att tgg ttc aat ggg gag atg gtt      48
Met Thr Thr Lys Lys Ala Asp Tyr Ile Trp Phe Asn Gly Glu Met Val
1               5                   10                  15 cgc tgg gaa gac gcg aag gtg cat gtg atg tcg cac gcg ctg cac tat      96
Arg Trp Glu Asp Ala Lys Val His Val Met Ser His Ala Leu His Tyr
                20                  25                  30 ggc act tcg gtt ttt gaa ggc atc cgt tgc tac gac tcg cac aaa gga     144
Gly Thr Ser Val Phe Glu Gly Ile Arg Cys Tyr Asp Ser His Lys Gly
            35                  40                  45 ccg gtt gta ttc cgc cat cgt gag cat atg cag cgt ctg cat gac tcc     192
Pro Val Val Phe Arg His Arg Glu His Met Gln Arg Leu His Asp Ser
        50                  55                  60 gcc aaa atc tat cgc ttc ccg gtt tcg cag agc att gat gag ctg atg     240
Ala Lys Ile Tyr Arg Phe Pro Val Ser Gln Ser Ile Asp Glu Leu Met
65                  70                  75                  80 gaa gct tgt cgt gac gtg atc cgc aaa aac aat ctc acc agc gcc tat     288
Glu Ala Cys Arg Asp Val Ile Arg Lys Asn Asn Leu Thr Ser Ala Tyr
                85                  90                  95 atc cgt ccg ctg atc ttc gtc ggt gat gtt ggc atg gga gta aac ccg     336
Ile Arg Pro Leu Ile Phe Val Gly Asp Val Gly Met Gly Val Asn Pro
            100                 105                 110 cca gcg gga tac tca acc gac gtg att atc gct gct ttc ccg tgg gga     384
Pro Ala Gly Tyr Ser Thr Asp Val Ile Ile Ala Ala Phe Pro Trp Gly
        115                 120                 125 gcg tat ctg ggc gca gaa gcg ctg gag cag ggg atc gat gcg atg gtt     432
Ala Tyr Leu Gly Ala Glu Ala Leu Glu Gln Gly Ile Asp Ala Met Val
    130                 135                 140 tcc tcc tgg aac cgc gca gca cca aac acc atc ccg acg gcg gca aaa     480
Ser Ser Trp Asn Arg Ala Ala Pro Asn Thr Ile Pro Thr Ala Ala Lys
145                 150                 155                 160 gcc ggt ggt aac tac ctc tct tcc ctg ctg gtg ggt agc gaa gcg cgc     528
Ala Gly Gly Asn Tyr Leu Ser Ser Leu Leu Val Gly Ser Glu Ala Arg
                165                 170                 175 cgc cac ggt tat cag gaa ggt atc gcg ctg gat gtg aac ggt tat atc     576
Arg His Gly Tyr Gln Glu Gly Ile Ala Leu Asp Val Asn Gly Tyr Ile
            180                 185                 190 tct gaa ggc gca ggc gaa aac ctg ttt gaa gtg aaa gat ggt gtg ctg     624
Ser Glu Gly Ala Gly Glu Asn Leu Phe Glu Val Lys Asp Gly Val Leu
        195                 200                 205 ttc acc cca ccg ttc acc tcc tcc gcg ctg ccg ggt att acc cgt gat     672
Phe Thr Pro Pro Phe Thr Ser Ser Ala Leu Pro Gly Ile Thr Arg Asp
    210                 215                 220 gcc atc atc aaa ctg gcg aaa gag ctg gga att gaa gta cgt gag cag     720
Ala Ile Ile Lys Leu Ala Lys Glu Leu Gly Ile Glu Val Arg Glu Gln
225                 230                 235                 240 gtg ctg tcg cgc gaa tcc ctg tac ctg gcg gat gaa gtg ttt atg tcc     768
Val Leu Ser Arg Glu Ser Leu Tyr Leu Ala Asp Glu Val Phe Met Ser
                245                 250                 255
```

```
ggt acg gcg gca gaa atc acg cca gtg cgc agc gta gac ggt att cag      816
Gly Thr Ala Ala Glu Ile Thr Pro Val Arg Ser Val Asp Gly Ile Gln
            260                 265                 270 gtt ggc gaa ggc cgt tgt ggc ccg gtt acc aaa cgc att cag caa gcc      864
Val Gly Glu Gly Arg Cys Gly Pro Val Thr Lys Arg Ile Gln Gln Ala
        275                 280                 285 ttc ttc ggc ctc ttc act ggc gaa acc gaa gat aaa tgg ggc tgg tta      912
Phe Phe Gly Leu Phe Thr Gly Glu Thr Glu Asp Lys Trp Gly Trp Leu
    290                 295                 300 gat caa gtt aat caa taa                                              930
Asp Gln Val Asn Gln
305
```

<210> SEQ ID NO 14
<211> LENGTH: 309
<212> TYPE: PRT
<213> ORGANISM: Escherichia coli

<400> SEQUENCE: 14

```
Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45

Pro Val Val Phe Arg His Arg Glu His Met Gln Arg Leu His Asp Ser
    50                  55                  60

Ala Lys Ile Tyr Arg Phe Pro Val Ser Gln Ser Ile Asp Glu Leu Met
65                  70                  75                  80

Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro
            100                 105                 110

Pro Ala Gly Tyr Ser Thr Asp Val Ile Ile Ala Ala Phe Pro Trp Gly
        115                 120                 125

Ala Tyr Leu Gly Ala Glu Ala Leu Glu Gln Gly Ile Asp Ala Met Val
    130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
            180                 185                 190

Ser Glu Gly Ala Gly Glu Asn Leu Phe Glu Val Lys Asp Gly Val Leu
        195                 200                 205

Phe Thr Pro Pro Phe Thr Ser Ser Ala Leu Pro Gly Ile Thr Arg Asp
    210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
        275                 280                 285

Phe Phe Gly Leu Phe Thr Gly Glu Thr Glu Asp Lys Trp Gly Trp Leu
```

Asp Gln Val Asn Gln
305

<210> SEQ ID NO 15
<211> LENGTH: 65
<212> TYPE: DNA
<213> ORGANISM: Artificial sequence
<220> FEATURE:
<223> OTHER INFORMATION: primer SVS 170

<400> SEQUENCE: 15
ctctagagga tccttaagaa ggagatatac catgaaaatg agtggcttta gcatagaaga    60
aaagg    65

<210> SEQ ID NO 16
<211> LENGTH: 35
<212> TYPE: DNA
<213> ORGANISM: Artificial sequence
<220> FEATURE:
<223> OTHER INFORMATION: primer SVS 169

<400> SEQUENCE: 16
gaattcgagc tcttattttg tctccttata agaaa    35

<210> SEQ ID NO 17
<211> LENGTH: 70
<212> TYPE: DNA
<213> ORGANISM: Artificial sequence
<220> FEATURE:
<223> OTHER INFORMATION: primer SVS 179

<400> SEQUENCE: 17
aatacgggcg ttagatttta caacgattgg tgattttttg ttcgctcaag ttagtataaa    60
aaagctgaac    70

<210> SEQ ID NO 18
<211> LENGTH: 72
<212> TYPE: DNA
<213> ORGANISM: Artificial sequence
<220> FEATURE:
<223> OTHER INFORMATION: primer SVS 180

<400> SEQUENCE: 18
tgatatcgcg cgatcttaat tgatgggtca tagttactcc tccttcagct gtttccttct    60
agacggccaa tg    72

<210> SEQ ID NO 19
<211> LENGTH: 70
<212> TYPE: DNA
<213> ORGANISM: Artificial sequence
<220> FEATURE:
<223> OTHER INFORMATION: primer SVS 192

<400> SEQUENCE: 19
cgaagtaagc ataaaaaaga tgcttaaggg atcacgtcta gacgctcaag ttagtataaa    60
aaagctgaac    70

<210> SEQ ID NO 20
<211> LENGTH: 70
<212> TYPE: DNA
<213> ORGANISM: Artificial sequence
<220> FEATURE:
<223> OTHER INFORMATION: primer SVS 193

```
<400> SEQUENCE: 20
cctgatattc atgtaagttc atgtgttctg tccatccttc cgctcacaat tccacacatt    60
atacgagccg                                                           70

<210> SEQ ID NO 21
<211> LENGTH: 70
<212> TYPE: DNA
<213> ORGANISM: Artificial sequence
<220> FEATURE:
<223> OTHER INFORMATION: primer SVS 199

<400> SEQUENCE: 21
tgttagcgta aaccaccaca taactatgga gcatctgcac cgctcaagtt agtataaaaa    60
agctgaacga                                                           70

<210> SEQ ID NO 22
<211> LENGTH: 70
<212> TYPE: DNA
<213> ORGANISM: Artificial sequence
<220> FEATURE:
<223> OTHER INFORMATION: primer SVS 200

<400> SEQUENCE: 22
cctcgataca ttgcggagaa aaattatatg gaagctttac tgaagcctgc ttttttatac    60
taagttggca                                                           70

<210> SEQ ID NO 23
<211> LENGTH: 35
<212> TYPE: DNA
<213> ORGANISM: Artificial sequence
<220> FEATURE:
<223> OTHER INFORMATION: primer ilvA5

<400> SEQUENCE: 23
gtcacgcata tggctgactc gcaacccctg tccgg                               35

<210> SEQ ID NO 24
<211> LENGTH: 35
<212> TYPE: DNA
<213> ORGANISM: Artificial sequence
<220> FEATURE:
<223> OTHER INFORMATION: primer ilvA3

<400> SEQUENCE: 24
cagtggatcc ttaacccgcc aaaaagaacc tgaac                               35

<210> SEQ ID NO 25
<211> LENGTH: 138
<212> TYPE: DNA
<213> ORGANISM: Artificial sequence
<220> FEATURE:
<223> OTHER INFORMATION: fragment containing Plac promoter flanked with
     SalI and HindIII

<400> SEQUENCE: 25
agatctgcgg gcagtgagcg caacgcaatt aatgtgagtt agctcactca ttaggcaccc    60
caggctttac actttatgct tccggctcgt ataatgtgtg gaattgtgag cggataacaa   120
tttcacacag gatctaga                                                 138

<210> SEQ ID NO 26
<211> LENGTH: 120
<212> TYPE: DNA
```

<213> ORGANISM: Artificial sequence
<220> FEATURE:
<223> OTHER INFORMATION: fragment attL

<400> SEQUENCE: 26

```
agatcttgaa gcctgctttt ttatactaag ttggcattat aaaaaagcat tgcttatcaa    60
tttgttgcaa cgaacaggtc actatcagtc aaaataaaat cattatttga tttcgaattc   120
```

<210> SEQ ID NO 27
<211> LENGTH: 40
<212> TYPE: DNA
<213> ORGANISM: Artificial sequence
<220> FEATURE:
<223> OTHER INFORMATION: primer P3

<400> SEQUENCE: 27

```
ctagtaagat cttgaagcct gctttttat actaagttgg                           40
```

<210> SEQ ID NO 28
<211> LENGTH: 41
<212> TYPE: DNA
<213> ORGANISM: Artificial sequence
<220> FEATURE:
<223> OTHER INFORMATION: primer P4

<400> SEQUENCE: 28

```
atgatcgaat tcgaaatcaa ataatgattt tattttgact g                        41
```

<210> SEQ ID NO 29
<211> LENGTH: 184
<212> TYPE: DNA
<213> ORGANISM: Artificial sequence
<220> FEATURE:
<223> OTHER INFORMATION: fragment attR

<400> SEQUENCE: 29

```
ctgcagtctg ttacaggtca ctaataccat ctaagtagtt gattcatagt gactgcatat    60
gttgtgtttt acagtattat gtagtctgtt ttttatgcaa aatctaattt aatatattga   120
tatttatatc atttacgtt tctcgttcag cttttttata ctaacttgag cgtctagaaa   180
gctt                                                                184
```

<210> SEQ ID NO 30
<211> LENGTH: 41
<212> TYPE: DNA
<213> ORGANISM: Artificial sequence
<220> FEATURE:
<223> OTHER INFORMATION: primer P5

<400> SEQUENCE: 30

```
atgccactgc agtctgttac aggtcactaa taccatctaa g                        41
```

<210> SEQ ID NO 31
<211> LENGTH: 46
<212> TYPE: DNA
<213> ORGANISM: Artificial sequence
<220> FEATURE:
<223> OTHER INFORMATION: primer P6

<400> SEQUENCE: 31

```
accgttaagc tttctagacg ctcaagttag tataaaaaag ctgaac                   46
```

<210> SEQ ID NO 32
<211> LENGTH: 38
<212> TYPE: DNA

```
<213> ORGANISM: Artificial sequence
<220> FEATURE:
<223> OTHER INFORMATION: primer P7

<400> SEQUENCE: 32
ttcttagacg tcaggtggca cttttcgggg aaatgtgc                              38

<210> SEQ ID NO 33
<211> LENGTH: 37
<212> TYPE: DNA
<213> ORGANISM: Artificial sequence
<220> FEATURE:
<223> OTHER INFORMATION: primer P8

<400> SEQUENCE: 33
taacagagat ctcgcgcaga aaaaaggat ctcaaga                                37

<210> SEQ ID NO 34
<211> LENGTH: 46
<212> TYPE: DNA
<213> ORGANISM: Artificial sequence
<220> FEATURE:
<223> OTHER INFORMATION: primer P9

<400> SEQUENCE: 34
aacagagatc taagcttaga tcctttgcct ggcggcagta gcgcgg                     46

<210> SEQ ID NO 35
<211> LENGTH: 35
<212> TYPE: DNA
<213> ORGANISM: Artificial sequence
<220> FEATURE:
<223> OTHER INFORMATION: primer P10

<400> SEQUENCE: 35
ataaactgca gcaaaaagag tttgtagaaa cgcaa                                 35

<210> SEQ ID NO 36
<211> LENGTH: 1388
<212> TYPE: DNA
<213> ORGANISM: Artificial sequence
<220> FEATURE:
<223> OTHER INFORMATION: DNA fragment containing Tc gene and ter_thrL

<400> SEQUENCE: 36
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
```

```
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc cgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
actagaaagc ttaacacaga aaaaagcccg cacctgacag tgcgggcttt ttttttcgac   1380
cactgcag                                                            1388
```

<210> SEQ ID NO 37
<211> LENGTH: 36
<212> TYPE: DNA
<213> ORGANISM: Artificial sequence
<220> FEATURE:
<223> OTHER INFORMATION: primer P11

<400> SEQUENCE: 37
agtaattcta gaaagcttaa cacagaaaaa agcccg                               36

<210> SEQ ID NO 38
<211> LENGTH: 43
<212> TYPE: DNA
<213> ORGANISM: Artificial sequence
<220> FEATURE:
<223> OTHER INFORMATION: primer P12

<400> SEQUENCE: 38
ctagtaggat ccctgcagtg gtcgaaaaaa aaagcccgca ctg                        43

<210> SEQ ID NO 39
<211> LENGTH: 828
<212> TYPE: DNA
<213> ORGANISM: Dactylosporangium sp.
<220> FEATURE:
<221> NAME/KEY: CDS
<222> LOCATION: (4)..(819)

<400> SEQUENCE: 39

```
cat atg tta acc ccg acc gaa ctc aaa caa tac cgt gaa gcc gga tat      48
    Met Leu Thr Pro Thr Glu Leu Lys Gln Tyr Arg Glu Ala Gly Tyr
    1               5                  10                  15 tta tta att gaa gat ggc ctc ggc cca cgt gaa gtt gac tgc tta cgt      96
Leu Leu Ile Glu Asp Gly Leu Gly Pro Arg Glu Val Asp Cys Leu Arg
                20                  25                  30 cgc gca gcc gcc gct ctg tac gcc cag gac tcg ccc gat cgc aca tta    144
Arg Ala Ala Ala Ala Leu Tyr Ala Gln Asp Ser Pro Asp Arg Thr Leu
            35                  40                  45 gaa aaa gat ggc cgc act gtt cgc gcc gtt cat ggc tgt cac cgc cgc    192
Glu Lys Asp Gly Arg Thr Val Arg Ala Val His Gly Cys His Arg Arg
        50                  55                  60 gac cct gtt tgt cgt gat tta gta cgt cac cct cgt tta ctt gga ccc    240
Asp Pro Val Cys Arg Asp Leu Val Arg His Pro Arg Leu Leu Gly Pro
    65                  70                  75 gca atg caa atc ctt tct ggt gac gtc tac gtt cat caa ttt aaa att    288
Ala Met Gln Ile Leu Ser Gly Asp Val Tyr Val His Gln Phe Lys Ile
80                  85                  90                  95
```

```
aac gca aaa gca cca atg act gga gat gtt tgg cct tgg cat cag gat      336
Asn Ala Lys Ala Pro Met Thr Gly Asp Val Trp Pro Trp His Gln Asp
            100                 105                 110 tac att ttt tgg gcc cgc gaa gat ggt atg gat cgc ccc cac gtt gtt      384
Tyr Ile Phe Trp Ala Arg Glu Asp Gly Met Asp Arg Pro His Val Val
        115                 120                 125 aat gta gcc gtt ctc tta gac gaa gca act cac tta aat gga cca tta      432
Asn Val Ala Val Leu Leu Asp Glu Ala Thr His Leu Asn Gly Pro Leu
    130                 135                 140 ctg ttt gtt ccc ggc act cac gaa ctc gga ttg att gat gta gaa cgt      480
Leu Phe Val Pro Gly Thr His Glu Leu Gly Leu Ile Asp Val Glu Arg
145                 150                 155 cgt gca cca gct ggc gac ggc gac gcc caa tgg ctc cca caa ctc tcc      528
Arg Ala Pro Ala Gly Asp Gly Asp Ala Gln Trp Leu Pro Gln Leu Ser
160                 165                 170                 175 gca gat tta gac tat gca att gat gcc gac ctg tta gcc cgt ctc acc      576
Ala Asp Leu Asp Tyr Ala Ile Asp Ala Asp Leu Leu Ala Arg Leu Thr
                180                 185                 190 gct ggc cgt ggt att gaa tca gca act ggc cca gca ggt tca atc tta      624
Ala Gly Arg Gly Ile Glu Ser Ala Thr Gly Pro Ala Gly Ser Ile Leu
            195                 200                 205 tta ttt gac tca cgt att gtt cac gga tct ggt acc aac atg tct ccc      672
Leu Phe Asp Ser Arg Ile Val His Gly Ser Gly Thr Asn Met Ser Pro
        210                 215                 220 cat ccc cgt ggt gta gtt ctt gtt aca tat aac cgt aca gat aac gcc      720
His Pro Arg Gly Val Val Leu Val Thr Tyr Asn Arg Thr Asp Asn Ala
    225                 230                 235 tta ccc gct caa gca gct ccc cgt cca gaa ttt tta gcc gca cgt gat      768
Leu Pro Ala Gln Ala Ala Pro Arg Pro Glu Phe Leu Ala Ala Arg Asp
240                 245                 250                 255 gca acc cca ctt gtc cct ctc ccc gca gga ttc gcc tta gct caa cct      816
Ala Thr Pro Leu Val Pro Leu Pro Ala Gly Phe Ala Leu Ala Gln Pro
                260                 265                 270 gta taaaagctt                                                        828
Val

<210> SEQ ID NO 40
<211> LENGTH: 272
<212> TYPE: PRT
<213> ORGANISM: Dactylosporangium sp.

<400> SEQUENCE: 40

Met Leu Thr Pro Thr Glu Leu Lys Gln Tyr Arg Glu Ala Gly Tyr Leu
1               5                   10                  15

Leu Ile Glu Asp Gly Leu Gly Pro Arg Glu Val Asp Cys Leu Arg Arg
            20                  25                  30

Ala Ala Ala Ala Leu Tyr Ala Gln Asp Ser Pro Asp Arg Thr Leu Glu
        35                  40                  45

Lys Asp Gly Arg Thr Val Arg Ala Val His Gly Cys His Arg Arg Asp
    50                  55                  60

Pro Val Cys Arg Asp Leu Val Arg His Pro Arg Leu Leu Gly Pro Ala
65                  70                  75                  80

Met Gln Ile Leu Ser Gly Asp Val Tyr Val His Gln Phe Lys Ile Asn
                85                  90                  95

Ala Lys Ala Pro Met Thr Gly Asp Val Trp Pro Trp His Gln Asp Tyr
            100                 105                 110

Ile Phe Trp Ala Arg Glu Asp Gly Met Asp Arg Pro His Val Val Asn
        115                 120                 125
```

-continued

```
Val Ala Val Leu Leu Asp Glu Ala Thr His Leu Asn Gly Pro Leu Leu
    130             135             140

Phe Val Pro Gly Thr His Glu Leu Gly Leu Ile Asp Val Glu Arg Arg
145             150             155                 160

Ala Pro Ala Gly Asp Gly Asp Ala Gln Trp Leu Pro Gln Leu Ser Ala
            165             170             175

Asp Leu Asp Tyr Ala Ile Asp Ala Asp Leu Leu Ala Arg Leu Thr Ala
            180             185             190

Gly Arg Gly Ile Glu Ser Ala Thr Gly Pro Ala Gly Ser Ile Leu Leu
        195             200             205

Phe Asp Ser Arg Ile Val His Gly Ser Gly Thr Asn Met Ser Pro His
    210             215             220

Pro Arg Gly Val Val Leu Val Thr Tyr Asn Arg Thr Asp Asn Ala Leu
225             230             235             240

Pro Ala Gln Ala Ala Pro Arg Pro Glu Phe Leu Ala Ala Arg Asp Ala
            245             250             255

Thr Pro Leu Val Pro Leu Pro Ala Gly Phe Ala Leu Ala Gln Pro Val
            260             265             270
```

US 8,524,476 B2

BACTERIUM PRODUCING A PRODUCT OF A REACTION CATALYZED BY A PROTEIN HAVING 2-OXOGLUTARATE-DEPENDENT ENZYME ACTIVITY AND A METHOD FOR MANUFACTURING THE PRODUCT

This application is a continuation under 35 U.S.C. §120 of PCT Patent Application No. PCT/JP2008/073914, filed Dec. 22, 2008, which claims priority under 35 U.S.C. §119 to Russian Patent Application No. 2007147436, filed on Dec. 21, 2007, which are incorporated in their entireties by reference. The Sequence Listing in electronic format filed herewith is also hereby incorporated by reference in its entirety (File Name: 2010-06-21T_US-351_Seq_List; File Size: 90 KB; Date Created: Jun. 21, 2010).

BACKGROUND OF THE INVENTION

1. Field of the Invention

The present invention relates to the microbiological industry, and specifically to a method for manufacturing a product of a reaction catalyzed by a protein having 2-oxoglutarate-dependent enzyme activity such as 4-hydroxy-L-isoleucine or a salt thereof using a bacterium transformed with a DNA fragment containing a gene coding for a protein having a 2-oxoglutarate-dependent enzyme such as L-isoleucine dioxygenase. This bacterium has also been modified to have enhanced expression of a gene coding for an L-isoleucine transporter, and has the ability to produce (2S,3R,4S)-4-hydroxy-L-isoleucine.

2. Brief Description of the Related Art 4-hydroxy-L-isoleucine is an amino acid which can be extracted and purified from fenugreek seeds (*Trigonella foenum-graecum L. leguminosae*). 4-hydroxy-L-isoleucine displays an insulinotropic activity, which is of great interest because of its stimulating effect which is clearly dependent on the plasma glucose concentration in the medium. This effect has been demonstrated both in isolated perfused rat pancreas and human pancreatic islets (Sauvaire, Y. et al, Diabetes, 47: 206-210, (1998)). Such a glucose dependency has not been confirmed for sulfonylurea (Drucker, D. J., Diabetes 47: 159-169, (1998)), which is the only insulinotropic drug currently used to treat type II diabetes [or non-insulin-dependent diabetes (NIDD) mellitus (NIDDM)], and as a consequence, hypoglycemia is still a common undesirable side effect of sulfonylurea treatment (Jackson, J., and Bessler, R. Drugs, 22: 211-245; 295-320, (1981); Jennings, A. et al. Diabetes Care, 12: 203-208, (1989)). Methods for improving tolerance to glucose are also known (Am. J. Physiol. Endocrinol., Vol. 287, E463-E471, 2004). This glucometabolism enhancement activity, and its potential application to pharmaceuticals and health foods, have been previously reported (Japanese Patent Application Laid-Open No. Hei 6-157302, US2007-000463A1).

4-hydroxy-L-isoleucine is only found in plants, and due to its particular insulinotropic action, might be considered a novel secretagogue with potential applications for the treatment of type II diabetes, which is characterized by defective insulin secretion associated with various degrees of insulin resistance (Broca, C. et al, Am. J. Physiol. 277 (Endocrinol. Metab. 40): E617-E623, (1999)).

Oxidizing iron, ascorbic acid, 2-oxyglutaric acid, and oxygen-dependent isoleucine by utilizing dioxygenase activity in fenugreek extract has been reported as a method for manufacturing 4-hydroxy-L-isoleucine (Phytochemistry, Vol. 44, No. 4, pp. 563-566, 1997). However, this method is unsatisfactory for manufacturing 4-hydroxy-L-isoleucine because the activity of the enzyme is inhibited by the substrate at isoleucine concentrations of 20 mM and above. Furthermore, the enzyme has not been identified, is derived from plant extracts, is not readily obtained in large quantities, and is unstable.

An efficient eight-step synthesis of optically pure (2S,3R, 4S)-4-hydroxyisoleucine with 39% overall yield has been disclosed. The key steps of this synthesis involve the biotransformation of ethyl 2-methylacetoacetate to ethyl(2S,3S)-2-methyl-3-hydroxy-butanoate with *Geotrichum candidum* and an asymmetric Strecker synthesis (Wang, Q. et al, Eur. J. Org. Chem., 834-839 (2002)).

A short six-step chemoenzymatic synthesis of (2S,3R,4S)-4-hydroxyisoleucine with total control of stereochemistry, the last step being the enzymatic resolution by hydrolysis of a N-phenylacetyl lactone derivative using the commercially available penicillin acylase G immobilized on Eupergit C(E-PAC), has also been disclosed (Rolland-Fulcrand, V. et al, J. Org. Chem., 873-877 (2004)).

But currently, there have been no reports of producing (2S,3R,4S)-4-hydroxy-L-isoleucine by using a bacterium transformed with a DNA fragment containing a gene coding for a protein having L-isoleucine dioxygenase activity; wherein the bacterium is also modified to have enhanced expression of a gene coding for L-isoleucine transporter and has the ability to produce (2S,3R,4S)-4-hydroxy-L-isoleucine.

Besides (2S,3R,4S)-4-hydroxy-L-isoleucine, products which are produced by reactions catalyzed by proteins having 2-oxoglutarate-dependent enzyme activity, and which are industrially important are known. However, there have been no reports of systems for efficiently producing the products by using the proteins having 2-oxoglutarate-dependent enzyme activity.

SUMMARY OF THE INVENTION

An aspect of present invention is to enhance production of a product of a reaction coupled with the formation of succinate from 2-oxoglutarate by a protein having 2-oxoglutarate-dependent enzyme activity. The product includes compounds in both the free form and a salt form thereof. Another aspect of the present invention is to provide a method for manufacturing the product by a reaction coupled with the formation of succinate from 2-oxoglutarate using a bacterium having 2-oxoglutarate-dependent enzyme activity. This bacterium has been modified to attenuate the expression of a gene coding for oxoglutarate dehydrogenase, preferably modified to attenuate the expression of genes coding for oxoglutarate dehydrogenase and isocitrate lyase, more preferably modified to attenuate the expression of genes coding for oxoglutarate dehydrogenase, isocitrate lyase, and isocitrate dehydrogenase phosphatase.

An aspect of present invention is to enhance production of (2S,3R,4S)-4-hydroxy-L-isoleucine, including both the free form and a salt form thereof. This compound may also be referred to as "(2S,3R,4S)-4HIL". Another aspect of the present invention is to provide a method for manufacturing (2S,3R,4S)-4-hydroxy-L-isoleucine or a salt thereof by direct enzymatic hydroxylation of L-isoleucine using a bacterium having L-isoleucine dioxygenase activity. This bacterium can over-express a gene coding for an L-isoleucine transporter, and is able to produce (2S,3R,4S)-4-hydroxy-L-isoleucine.

A bacterium has previously been isolated from nature having a high level of L-isoleucine dioxygenase activity, and a gene was cloned which encodes L-isoleucine dioxygenase. It was found that L-isoleucine dioxygenase may be used in the synthesis of (2S,3R,4S)-4-hydroxy-L-isoleucine.

Another aspect of the present invention includes providing a method for enhanced production of (2S,3R,4S)-4-hydroxy-L-isoleucine using a bacterium having L-isoleucine dioxygenase activity. The above aspect was achieved by finding that a bacterium having L-isoleucine dioxygenase activity produced more (2S,3R,4S)-4-hydroxy-L-isoleucine if the bacterium is modified to overexpress a gene coding for an L-isoleucine transporter.

It is an aspect of the present invention to provide a bacterium transformed with a DNA fragment comprising a gene coding for a protein having L-isoleucine dioxygenase enzymatic activity, wherein said bacterium has been modified to overexpress a gene coding for an L-isoleucine transporter, and wherein said bacterium is able to produce (2S,3R,4S)-4-hydroxy-L-isoleucine.

It is a further aspect of the present invention to provide the (2S,3R,4S)-4HIL-producing bacterium as described above, wherein the gene coding for a protein having L-isoleucine dioxygenase activity is selected from the group consisting of:
  (a) a DNA comprising the nucleotide sequence of SEQ ID No: 1;
  (b) a DNA that hybridizes under stringent conditions with a DNA comprising a nucleotide sequence complementary to the nucleotide sequence of SEQ ID No: 1, and wherein said DNA encodes a protein having L-isoleucine dioxygenase activity;
  (c) a DNA comprising a nucleotide sequence that encodes a protein comprising the amino acid sequence of SEQ ID No: 2;
  (d) a DNA comprising a nucleotide sequence that encodes a protein comprising an amino acid sequence of SEQ ID NO. 2, except that said amino acid sequence contains a substitution, deletion, insertion, addition, or inversion of one or several amino acid residues, and wherein said protein has L-isoleucine dioxygenase activity; and
  (e) a DNA comprising a nucleotide sequence that encodes a protein comprising an amino acid sequence that is at least 98% homologous to the amino acid sequence of SEQ ID NO: 2, and wherein said protein has L-isoleucine dioxygenase activity.

It is a further aspect of the present invention to provide the (2S,3R,4S)-4HIL-producing bacterium as described above, wherein the bacterium has been modified to enhance the activity of L-isoleucine dioxygenase.

It is a further aspect of the present invention to provide the (2S,3R,4S)-4HIL-producing bacterium as described above, wherein the activity of L-isoleucine dioxygenase is enhanced by increasing the expression of the gene encoding L-isoleucine dioxygenase.

It is a further aspect of the present invention to provide the (2S,3R,4S)-4HIL-producing bacterium as described above, wherein the expression of L-isoleucine dioxygenase is increased by modifying an expression control sequence of the gene encoding L-isoleucine dioxygenase or by increasing the copy number of the gene encoding L-isoleucine dioxygenase.

It is a further aspect of the present invention to provide (2S,3R,4S)-4HIL-producing the bacterium as described above, wherein the gene coding for the L-isoleucine transporter is the brnQ gene from *Escherichia coli*.

It is a further aspect of the present invention to provide the bacterium as described above, wherein the bacterium has additionally been modified to attenuate the expression of genes coding for oxoglutarate dehydrogenase, isocitrate lyase, and isocitrate dehydrogenase phosphatase.

It is a further aspect of the present invention to provide the bacterium as described above, wherein said expression is attenuated by inactivating said genes.

It is a further aspect of the present invention to provide the bacterium as described above, wherein the bacterium has additionally been modified to attenuate the expression of a gene coding for a branched-chain amino-acid aminotransferase.

It is a further aspect of the present invention to provide the bacterium as described above, wherein said expression is attenuated by inactivating said gene.

It is a further aspect of the present invention to provide the bacterium as described above, wherein the bacterium belongs to a genus selected from the group consisting of *Escherichia, Pseudomonas, Corynebacterium, Arthrobacter, Aspergillus*, and *Bacillus*.

It is a further aspect of the present invention to provide the bacterium as described above, wherein the bacterium is selected from the group consisting of *Escherichia coli, Arthrobacter simplex, Corynebacterium glutamicum, Arthrobacter globiformis, Arthrobacter sulfureus, Arthrobacter viscosus*, and *Bacillus subtilis*.

It is a further aspect of the present invention to provide a method for manufacturing (2S,3R,4S)-4-hydroxy-L-isoleucine or a salt thereof, comprising:
  cultivating the (2S,3R,4S)-4HIL-producing bacterium as described above in a culture medium containing L-isoleucine; and
  isolating (2S,3R,4S)-4-hydroxy-L-isoleucine.

It is a further aspect of the present invention to provide the method as described above, wherein the culture medium comprises a carbon source selected from the group consisting of a carbohydrate and an alcohol.

It is a further aspect of the present invention to provide the method as described above, wherein said carbohydrate is glucose and said alcohol is glycerol.

An aspect of present invention is to enhance production of 4-hydroxy-L-proline, including both the free form and a salt form thereof. Another aspect of the present invention is to provide a method for manufacturing 4-hydroxy-L-prolinee or a salt thereof by direct enzymatic hydroxylation of L-proline using a bacterium having L-proline hydroxylase activity.

The present invention is described in detail below.

DESCRIPTION OF THE PREFERRED EMBODIMENTS

1. Bacterium

Figure 1:
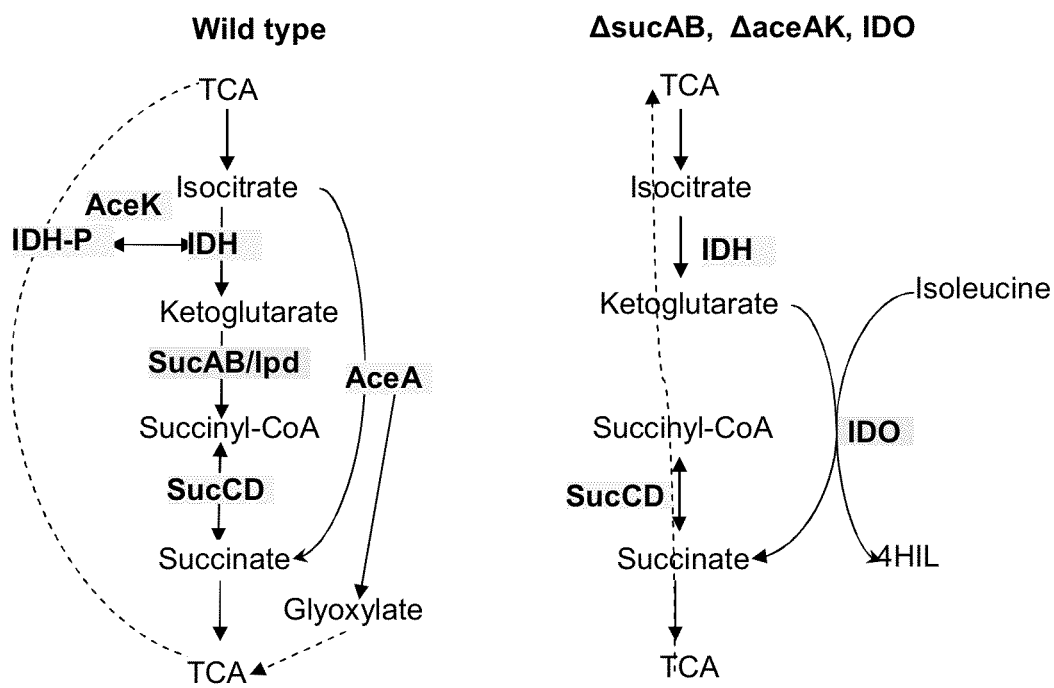
FIG. 1 shows 'shunting' of the TCA cycle in the strain MG1655 (ΔsucAB, ΔaceAK, $P_L$-brnQ)_[pELAC-IDO(Lys, 23)] due to simultaneous oxidation of isoleucine and α-ketoglutarate (2-oxoglutarate).

The term "bacterium" can include an enzyme-producing bacteria, a mutant, and a genetic recombinant of such bacteria in which the targeted enzymatic activity is present or has been enhanced, and the like.

The term "2-oxoglutarate-dependent enzyme activity" can refer to an enzymatic activity to catalyze a reaction coupled with the formation of succinate from 2-oxoglutarate.

A number of proteins having 2-oxoglutarate-dependent enzyme activity, such as 2-oxoglutarate-dependent dioxygenases have been reported. Other examples include dioxygenases used in the production of useful products, such as a Pro hydroxylase which converts L-Pro to hydroxy-Pro (APPLIED AND ENVIRONMENTAL MICROBIOLOGY, September 1999, p. 4028-4031), a γ-butyrobetaine hydroxylase converting γ-butyrobetaine to L-Carnitine (WO2005/083089). Besides these dioxygenases, a number of dioxygeneases have been reported. For example, refer to: Critical Reviews in Biochemistry and Molecular Biology, 39:21-68, 2004 and NATURE CHEMICAL BIOLOGY, 4 NUMBER 3 March: 152-156, 2008. As for the 2-oxoglutarate-dependent dioxygenases described in the reviews, the bacterium has been modified to attenuate the expression of a gene coding for an oxoglutarate dehydrogenase (such as ΔsucAB, ΔsucA, ΔsucB), and can be modified to attenuate the expression of genes coding for oxoglutarate dehydrogenase and isocitrate lyase (such as ΔsucAB, ΔsucA, or ΔsucB, plus ΔaceA), and can be further modified to attenuate the expression of genes coding for oxoglutarate dehydrogenase, isocitrate lyase, and isocitrate dehydrogenase phosphatase (such as ΔsucAB, ΔsucA, or ΔsucB, plus ΔaceAK), which is represented by *E. coli* strain MG1655 (ΔsucAB, ΔaceAK) which is described in the Examples, and is considered to be a general host for efficiently using 2-oxoglutarate produced from a carbon source such as D-glucose, in 2-oxoglutarate-dependent enzyme reactions.

As an example, the protein having 2-oxoglutarate-dependent enzyme activity can be a protein having L-isoleucine dioxygenase activity, and the product of the reaction catalyzed by the protein can be (2S,3R,4S)-4-hydroxy-L-isoleucine. However, the present invention is not limited to this example.

The term "(2S,3R,4S)-4-hydroxy-L-isoleucine" or "(2S,3R,4S)-4HIL" or "4HIL" refers to a single chemical compound or a mixture of compounds containing (2S,3R,4S)-4-hydroxyisoleucine.

The term "bacterium" can include an enzyme-producing bacterium, a mutant, and a genetic recombinant of such bacterium in which the targeted enzymatic activity is present or has been enhanced, and the like.

L-isoleucine dioxygenase from microbial cells may be abbreviated "IDO."

Screening of environmental microorganisms revealed a unique microbe *Bacillus thuringiensis* strain 2-e-2, which possesses an activity of catalyzing a reaction in which (2S,3R,4S)-4HIL is directly formed from L-isoleucine, both the free form and a salt form thereof. The novel L-isoleucine dioxygenase was purified from the cultivated microbial cells, and may be abbreviated a "IDO(Lys,23)."

Furthermore, the N-terminal amino acid sequence of IDO (Lys,23) was determined by purifying dioxygenase derived from of *Bacillus thuringiensis* strain 2-e-2. *Bacillus thuringiensis* strain 2-e-2 was named *Bacillus thuringiensis* AJ110584 and deposited at the International Patent Organism Depositary, National Institute of Advanced Industrial Science and Technology (Central 6, 1-1, Higashi 1-chome, Tsukuba, Ibaraki 305-8566, Japan) on Sep. 27, 2006 and given an accession number of FERM BP-10688 under the provisions of Budapest Treaty.

The DNA encoding IDO(Lys,23) is shown in SEQ ID No: 1. Furthermore, the amino acid sequence of IDO(Lys,23) encoded by the nucleotide sequence of SEQ ID NO: 1 is shown in SEQ ID No: 2. SEQ ID NO: 2 is the amino acid sequence of IDO(Lys,23) encoded by the nucleotide sequence of SEQ ID NO: 1. IDO(Lys,23) of SEQ ID NO: 2 possesses L-isoleucine dioxygenase activity, and catalyzes the reaction in which (2S,3R,4S)-4HIL shown in the following formula (I) is directly synthesized from one molecule of L-isoleucine.

(I)

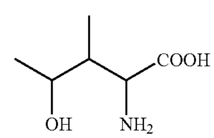

A DNA that encodes IDO which catalyzes the reaction in which (2S,3R,4S)-4HIL is formed from L-isoleucine is not only the DNA shown in SEQ ID No: 1. This is because there may be differences in nucleotide sequences from each species and strains among *Bacillus* that form IDO which catalyzes the reaction of producing (2S,3R,4S)-4HIL from L-isoleucine.

The DNA not only includes the isolated DNA encoding IDO, but also a DNA in which mutations have been artificially added to the DNA that encodes IDO. This DNA may be isolated from the chromosome of an IDO-producing microorganism. The DNA encodes IDO that is able to catalyze the above-described reaction. Methods for artificially adding mutations include typically used methods for introducing site-specific mutations, such as those described in Method. in Enzymol., 154 (1987).

A DNA that hybridizes under stringent conditions with a DNA having a nucleotide sequence complementary to the nucleotide sequence of SEQ ID No: 1, and encodes a protein having IDO activity is also included in the above-described DNA. The term "stringent conditions" can refer to conditions under which a specific hybrid is formed and a non-specific hybrid is not formed. Although it is difficult to numerically express these conditions explicitly, by way of example, these conditions include those under which DNA molecules having higher homology e.g. such 70% or more, or in another example 80% or more, or in another example 90% or more, and in another example 95% or more homology, hybridize with each other, while DNA molecules having lower homology do not hybridize with each other, or those under which hybridization occurs under typical washing conditions in Southern hybridization, that is, at a salt concentration corresponding to 0.1×SSC and 0.1% SDS at 37° C., or in another example 0.1×SSC and 0.1% SDS at 60° C., and in another example 0.1×SSC and 0.1% SDS at 65° C. The length of the probe may be suitably selected, depending on the hybridization conditions, and usually varies from 100 bp to 1 kbp. Furthermore, "L-isoleucine dioxygenase activity" may be described as the activity that synthesizes (2S,3R,4S)-4HIL from L-isoleucine. However, when a nucleotide sequence that hybridizes under stringent conditions with a nucleotide sequence complementary to the nucleotide sequence of SEQ ID No: 1, it can retain L-isoleucine dioxygenase activity of 10% or more, or in another example 30% or more, or in another example 50% or more, and in another example 70% or more, of the protein having the amino acid sequence of SEQ ID No: 2 at 37° C. and pH 8.

Furthermore, a DNA encoding a protein which is substantially identical to the IDO encoded by the DNA of SEQ ID No: 1 is also included in the above-described DNA. Namely, the following DNAs are also included:

(a) a DNA of the nucleotide sequence of SEQ ID No: 1;
(b) a DNA that hybridizes under stringent conditions with a DNA having a nucleotide sequence complementary to the nucleotide sequence of SEQ ID No: 1 and encodes a protein having L-isoleucine dioxygenase activity;
(c) a DNA that encodes a protein of the amino acid sequence of SEQ ID No: 2;
(d) a DNA that encodes a protein having an amino acid sequence that contains a substitution, deletion, insertion, addition or inversion of one or several amino acid residues in the amino acid sequence of SEQ ID No: 2 and having the L-isoleucine dioxygenase activity; and
(e) a DNA that encodes a protein having an amino acid sequence that is at least 70% homologous, or in another example at least 80% homologous, or in another example at least 90% homologous and still in another example at least 95% homologous to the amino acid sequence of SEQ ID NO:2 and has L-isoleucine dioxygenase activity.

Here, "one or several" refers to the number of changes which do not result in significant changes to the 3D structure of the protein, or a significant reduction of the L-isoleucine dioxygenase activity, and more specifically, can be in the range of 1 to 78, or in another example 1 to 52, or in another example 1 to 26, and still in another example 1 to 13.

The substitution, deletion, insertion, addition, or inversion of one or several amino acid residues should be conservative mutation(s) so that the activity is maintained. The representative conservative mutation is a conservative substitution. Examples of conservative substitutions include substitution of Ala with Ser or Thr, substitution of Arg with Gln, His or Lys, substitution of Asn with Glu, Gln, Lys, His or Asp, substitution of Asp with Asn, Glu or Gln, substitution of Cys with Ser or Ala, substitution of Gln with Asn, Glu, Lys, His, Asp or Arg, substitution of Glu with Asn, Gln, Lys or Asp, substitution of Gly with Pro, substitution of His with Asn, Lys, Gln, Arg or Tyr, substitution of Ile with Leu, Met, Val or Phe, substitution of Leu with Ile, Met, Val or Phe, substitution of Lys with Asn, Glu, Gln, His or Arg, substitution of Met with Ile, Leu, Val or Phe, substitution of Phe with Trp, Tyr, Met, Ile or Leu, substitution of Ser with Thr or Ala, substitution of Thr with Ser or Ala, substitution of Trp with Phe or Tyr, substitution of Tyr with His, Phe or Trp, and substitution of Val with Met, Ile or Leu.

Furthermore, "L-isoleucine dioxygenase activity" refers to the synthesis of the (2S,3R,4S)-4HIL from L-isoleucine as described above. However, when the amino acid sequence of SEQ ID No: 2 contains a substitution, deletion, insertion, addition, or inversion of one or several amino acid residues, it can retain L-isoleucine dioxygenase activity of 10% or more, or in another example 30% or more, or in another example 50% or more, and still in another example 70% or more, as compared to the protein having the amino acid sequence of SEQ ID No: 2 under conditions of 30° C. and pH 6.0. The L-isoleucine dioxygenase activity of the IDO can be measured by analysis of (2S,3R,4S)-4HIL formation from L-isoleucine by using high-performance liquid chromatography (HPLC).

Furthermore, a homologue DNA of SEQ ID NO: 1 can be used as the gene encoding L-isoleucine dioxygenase. Whether the homologue DNA encodes L-isoleucine dioxygenase or not can be confirmed by measuring L-isoleucine dioxygenase activity of the cell lysate, or cell lysate of the microorganism in which the homologue DNA is overexpressed.

The homologue DNA of SEQ ID NO: 1 can also be prepared from the genome of another *Bacillus* species, for example, *Bacillus cereus, Bacillus weihenstephanensis*.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* can include, but are not limited to, *Escherichia coli (E. coli)*.

The bacterium belonging to the genus *Escherichia* is not particularly limited; however, e.g., bacteria described by Neidhardt, F. C. et al. (*Escherichia coli* and *Salmonella typhimurium*, American Society for Microbiology, Washington D.C., 1208, Table 1) can be used.

The phrase "a bacterium belonging to the genus *Pseudomonas*" means that the bacterium is classified into the genus *Pseudomonas* according to the classification known to a person skilled in the art of microbiology.

The phrase "a bacterium belonging to the genus *Corynebacterium*" means that the bacterium is classified into the genus *Corynebacterium* according to the classification known to a person skilled in the art of microbiology. Examples of a bacterium belonging to the genus *Corynebacterium* can include, but are not limited to, *Corynebacterium glutamicum*.

The phrase "a bacterium belonging to the genus *Arthrobacter*" means that the bacterium is classified into the genus *Arthrobacter* according to the classification known to a person skilled in the art of microbiology. Examples of a bacterium belonging to the genus *Arthrobacter* can include, but are not limited to, *Arthrobacter simplex, Arthrobacter globiformis, Arthrobacter sulfureus*, and *Arthrobacter viscosus*.

The phrase "a bacterium belonging to the genus *Aspergillus*" means that the bacterium is classified into the genus *Aspergillus* according to the classification known to a person skilled in the art of microbiology.

The phrase "a bacterium belonging to the genus *Bacillus*" means that the bacterium is classified into the genus *Bacillus* according to the classification known to a person skilled in the art of microbiology. Examples of a bacterium belonging to the genus *Bacillus* can include, but are not limited to, *Bacillus subtilis*.

The brnQ gene from *E. coli* (synonyms—ECK0395, b0401, hrbA) encodes the branched chain amino acid LIVCS transporter BrnQ (synonyms—B0401, HrbA, LIV-II). The brnQ gene (nucleotides 418815 to 420134; GenBank accession no. NC_000913.2; gi: 16128105) is located between the gene phoR and the gene proY on the chromosome of *E. coli* K-12. The nucleotide sequence of the brnQ gene and the amino acid sequence of the BrnQ protein encoded by the brnQ gene are shown in SEQ ID NO: 3 and SEQ ID NO: 4, respectively.

The sucA gene from *E. coli* (synonyms—ECK0714, lys, b0726, lys+met) encodes a subunit of the E1(0) component of the oxoglutarate dehydrogenase complex—SucA (synonyms—B0726, Lys). The sucA gene (nucleotides 757,929 to 760,730; GenBank accession no. NC_000913.2; gi: 16128105) is located between the gene G6388, partially overlapping with it, and the gene sucB on the chromosome of *E. coli* K-12. The nucleotide sequence of the sucA gene and the amino acid sequence of the SucA protein encoded by the sucA gene are shown in SEQ ID NO: 5 and SEQ ID NO: 6, respectively.

The sucB gene from *E. coli* (synonyms—ECK0715, b0727) encodes a subunit of the E2(0) component of the oxoglutarate dehydrogenase complex—SucB (synonym B0727). The sucB gene (nucleotides 760,745 to 761,962; GenBank accession no. NC_000913.2; gi: 16128105) is located between the gene sucA and the gene sucC on the chromosome of *E. coli* K-12. The nucleotide sequence of the sucB gene and the amino acid sequence of the SucB protein encoded by the sucB gene are shown in SEQ ID NO: 7 and SEQ ID NO: 8, respectively.

The aceA gene from *E. coli* (synonyms—ECK4007, b4015, icl) encodes a subunit of the isocitrate lyase—AceA (synonym B4015, Id). The aceA gene (nucleotides 4,215,132 to 4,216,436; GenBank accession no. NC_000913.2; gi: 16128105) is located between the gene aceB and the gene aceK on the chromosome of *E. coli* K-12. The nucleotide sequence of the aceA gene and the amino acid sequence of the AceA protein encoded by the aceA gene are shown in SEQ ID NO: 9 and SEQ ID NO: 10, respectively.

The aceK gene from *E. coli* (synonyms—ECK4008, b4016) encodes a subunit of the isocitrate dehydrogenase phosphatase—AceK (synonym B4016). The aceK gene (nucleotides 4,216,619 to 4,218,355; GenBank accession no. NC_000913.2; gi: 16128105) is located between the gene aceA and the gene arpA, that is oriented in opposite direction, and partially overlapping with it, on the chromosome of *E. coli* K-12. The nucleotide sequence of the aceK gene and the amino acid sequence of the AceK protein encoded by the aceK gene are shown in SEQ ID NO: 11 and SEQ ID NO: 12, respectively.

The ilvE gene from *E. coli* (synonyms—ECK3762, b3770) encodes a subunit of the branched-chain amino-acid aminotransferase—IlvE (synonym B3770). The ilvE gene (nucleotides 3,950,507 to 3,951,436; GenBank accession no. NC_000913.2; gi: 16128105) is located between the gene ilvM and the gene ilvD on the chromosome of *E. coli* K-12. The nucleotide sequence of the ilvE gene and the amino acid sequence of the IlvE protein encoded by the ilvE gene are shown in SEQ ID NO: 13 and SEQ ID NO: 14, respectively.

Since there may be some differences in DNA sequences between the genera or strains of the *Escherichia* genus, the brnQ gene with enhanced expression, or the sucA, sucB, aceA, aceK, ilvE genes with attenuated expression are not limited to the genes shown in SEQ ID No: 3, SEQ ID No: 5, SEQ ID No: 7, SEQ ID No: 9, SEQ ID No: 11 and SEQ ID No: 13, but may include genes which are homologous to SEQ ID No: 3, SEQ ID No: 5, SEQ ID No: 7, SEQ ID No: 9, SEQ ID No: 11 and SEQ ID No: 13, but which encode a variant protein of the BrnQ, SucA, SucB, AceA, AceK and IlvE proteins, respectively. The phrase "variant protein" can mean a protein which has changes in the sequence, whether they are deletions, insertions, additions, or substitutions of amino acids, but the activity as the BrnQ/SucA/SucB/AceA/AceK/IlvE protein is maintained. The number of changes in the variant protein depends on the position or the type of amino acid residues in the three dimensional structure of the protein. It may be 1 to 30, or in another example 1 to 15, and in another example 1 to 5 in SEQ ID No: 4, SEQ ID No: 6, SEQ ID No: 8, SEQ ID No: 10, SEQ ID No: 12 and SEQ ID No: 14. These changes in the variants can occur in regions of the protein which are not critical for the function of the protein. This is because some amino acids have high homology to one another so the three dimensional structure or activity is not affected by such a change. Therefore, the protein variant encoded by the brnQ/sucA/sucB/aceA/aceK/ilvE gene may be one which has a homology of not less than 80%, or in another example than 90%, and in another example not less than 95%, with respect to the entire amino acid sequence shown in SEQ ID No: 4, SEQ ID No: 6, SEQ ID No: 8, SEQ ID No: 10, SEQ ID No: 12 and SEQ ID No: 14, as long as the activity of the BrnQ, SucA, SucB, AceA, AceK and IlvE proteins, respectively, is maintained (prior to inactivation of the sucA/sucB/aceA/aceK/ilvE gene).

Homology between two amino acid sequences can be determined using well-known methods, for example, the computer program BLAST 2.0, which calculates three parameters: score, identity and similarity.

Moreover, the brnQ/sucA/sucB/aceA/aceK/ilvE gene may be a variant which hybridizes under stringent conditions with the nucleotide sequence shown in SEQ ID No: 3/SEQ ID No: 5/SEQ ID No: 7/SEQ ID No: 9/SEQ ID No: 11/SEQ ID No: 13, or a probe which can be prepared from the nucleotide sequence under stringent conditions, provided that it encodes a functional BrnQ/SucA/SucB/AceA/AceK/IlvE protein prior to inactivation. "Stringent conditions" can include those under which a specific hybrid, for example, a hybrid having homology of not less than 60%, or in another example not less than 70%, or in another example not less than 80%, still in another example not less than 90%, and even in another example not less than 95%, is formed and a non-specific hybrid, for example, a hybrid having homology lower than the above, is not formed. For example, stringent conditions are exemplified by washing one time or more, or in another example two or three times at a salt concentration of 1×SSC, 0.1% SDS, or in another example 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Washing may be performed 2 to 3 times. The length of the probe may be suitably selected depending on the hybridization conditions, and is usually 100 bp to 1 kbp.

The phrase "enhanced expression of the gene" or "overexpression of a gene" can mean that the expression of the gene is higher than that of a non-modified strain, for example, a wild-type strain. Examples of such modification include increasing the copy number of expressed gene per cell, increasing the expression level of the gene, and so forth. The quantity of the copy number of an expressed gene can be measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like. The amount of the protein encoded by the gene can be measured by known methods including SDS-PAGE followed by immunoblotting assay (Western blotting analysis), and the like. Furthermore, wild-type strains that can act as a control include, for example, *Escherichia coli* K-12.

The phrase "[t]ransformation of a bacterium with DNA encoding a protein" can mean introduction of the DNA into a bacterium, for example, by conventional methods. Transformation of this DNA will result in an increase in expression of the gene encoding the protein(s), and will enhance the activity of the protein in the bacterial cell. Methods of transformation can include any known methods that have hitherto been reported. For example, a method of treating recipient cells with calcium chloride so as to increase permeability of the cells to DNA has been reported for *Escherichia coli* K-12 (Mandel, M. and Higa, A., *J. Mol. Biol.*, 53, 159 (1970)) may be used.

Methods of overexpressing a gene, or enhancing the expression of a gene include increasing the gene copy number. Introducing a gene into a vector that is able to function in a bacterium of the *Escherichia* genus increases the copy number of the gene. The low-copy vectors can be used. Examples of low-copy vectors include but are not limited to pSC101, pMW118, pMW119, and the like. The term "low copy vector" is used for vectors, the copy number of which is up to 5 copies per cell.

Enhancement of gene expression may also be achieved by introduction of multiple copies of the gene into a bacterial chromosome by, for example, homologous recombination, Mu integration, or the like. For example, one act of Mu integration allows for introduction of up to 3 copies of the gene into a bacterial chromosome.

Increasing the copy number of a gene can also be achieved by introducing multiple copies of the gene into the chromosomal DNA of the bacterium. In order to introduce multiple copies of the gene into a bacterial chromosome, homologous recombination can be carried out using a sequence which is present in multiple copies as targets in the chromosomal DNA. Sequences having multiple copies in the chromosomal DNA can include, but are not limited to repetitive DNA, or inverted repeats present at the end of a transposable element.

Enhancing gene expression can also be achieved by placing the objective DNA under the control of a potent promoter. For example, the $P_{tac}$ promoter, the lac promoter, the trp promoter, the trc promoter, the $P_R$, or the $P_L$ promoters of lambda phage are all known examples of potent promoters. The use of a potent promoter can be combined with the multiplication of gene copies.

Alternatively, the effect of a promoter can be enhanced by, for example, introducing a mutation into the promoter to increase the transcription level of a gene located downstream of the promoter. Furthermore, it is known that substitution of several nucleotides in the spacer between ribosome binding site (RBS) and the start codon, especially the sequences immediately upstream of the start codon, can profoundly affect the mRNA translatability.

Moreover, it is also possible to introduce a nucleotide substitution into a promoter region of a gene on the bacterial chromosome, which results in stronger promoter function. The alteration of the expression control sequence can be performed, for example, in the same manner as the gene substitution using a temperature-sensitive plasmid, as disclosed in International Patent Publication WO 00/18935 and Japanese Patent Application Laid-Open No. 1-215280.

It was proposed that attenuating expression of the sucA, sucB, aceA and aceK genes should lead to 'shunting' of the TCA cycle in mutant cells due to simultaneous oxidation of isoleucine and α-ketoglutarate (2-oxoglutarate), and may result in enhanced production of 4HIL. At the same time, simultaneous oxidation of isoleucine and α-ketoglutarate by IDO activity will be necessary for both growth of the bacterium and stabilization of the plasmid carrying a gene encoding IDO. In other words, the process of isoleucine hydroxylation will be necessary for cell growth. In this case, the biotransformation of isoleucine into 4-HIL can be achieved during bacterial cell growth without supplementing with antibiotics. This strategy was achieved by constructing a strain which lacks succinyl-CoA due to deletion of sucAB and aceAK genes (FIG. 1, Examples 3-5). This principle can be applied to any reaction which is coupled with the formation of succinate from 2-oxoglutarate. Furthermore, the minimum requirement is attenuating the expression of the gene coding for oxoglutarate dehydrogenase (such as ΔsucAB, ΔsucA, ΔsucB). Preferably the bacterium is further modified to attenuate the expression of the gene coding for isocitrate lyase (such as ΔaceA). Also, the bacterium is further modified to attenuate the expression of the genes coding for isocitrate lyase, and isocitrate dehydrogenase phosphatase (such as ΔaceAK).

By attenuating the expression of the gene coding for oxoglutarate dehydrogenase, the metabolism of 2-oxoglutarate is suppressed and the supply of 2-oxoglutarate to the 2-oxoglutarate-dependent enzyme is enhanced in the cells. The thus-engineered bacterium is then a host suitable for conducting 2-oxoglutarate-dependent enzyme reactions. The attenuation of the gene coding for oxoglutarate dehydrogenase increases 2-oxoglutarate levels in the cells and thereby renders the supply thereof to a 2-oxoglutarate-dependent enzyme to be efficient. The oxoglutarate dehydrogenase converts 2-oxoglutarate to succinyl-CoA in the TCA cycle The attenuation of the gene coding for isocitrate lyase catalyzing the conversion of isocitrate to succinate in the glyoxylate cycle further increases the supply of 2-oxoglutarate. By this combination, the pathways from 2-oxoglutarate to succinate in the TCA and glyoxylate cycles are blocked, thereby further increasing the supply of 2-oxoglutarate to the 2-oxoglutarate-dependent enzyme. The attenuation of the gene coding for isocitrate dehydrogenease phosphatase further suppresses the inactivation of isocitrate dehydrogenase producing 2-oxoglutrate from isocitate. As the branched-chain amino acid aminotransferase deaminate 4HIL (Smirnov S. V. et al, FEMS Microbiol Lett.; 273(1):70-7 (2007)), expression of the ilvE gene can be attenuated, and should lead to higher yields of 4HIL due to the prevention of deamination of 4HIL.

The phrase "bacterium has been modified to attenuate expression the gene" can mean that the bacterium has been modified in such a way that the modified bacterium contains a reduced amount of the protein encoded by the gene as compared with an unmodified bacterium, or the modified bacterium is unable to synthesize the protein. The phrase "bacterium has been modified to attenuate expression of the gene" can also mean that the bacterium has been modified in such a way that the modified gene encodes a mutant protein with decreased activity.

The presence or absence of the gene in the chromosome of a bacterium can be detected by well-known methods, including PCR, Southern blotting, and the like.

The phrase "inactivation of the gene" can mean that the modified gene encodes a completely inactive protein. It is also possible that the modified DNA region is unable to naturally express the gene due to deletion of a part of or the entire gene, the shifting of the reading frame of the gene, the introduction of missense/nonsense mutation(s), or the modification of an adjacent region of the gene, including sequences controlling gene expression, such as promoter(s), enhancer(s), attenuator(s), ribosome-binding site(s), etc.

Expression of the gene can be attenuated by introducing a mutation into the gene on the chromosome so that intracellular activity of the protein encoded by the gene is decreased as compared with an unmodified strain. Such a mutation on the gene can be replacement of one base or more to cause an amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein having a decreased activity can be prepared, and a bacterium can be transformed with a DNA fragment containing the mutant gene. Then, the native gene on the chromosome can be replaced with the mutant gene by homologous recombination, and the resulting strain can be selected. Such gene replacement using homologous recombination can be conducted by the method employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. No. 6,303,383 or JP 05-007491A). Furthermore, the incorporation of a site-specific mutation by gene substitution using homologous recombination such as set forth above can also be conducted with a plasmid which is unable to replicate in the host.

Expression of the gene can also be attenuated by insertion of a transposon or an IS factor into the coding region of the gene (U.S. Pat. No. 5,175,107), or by conventional methods, such as mutagenesis treatment by UV irradiation or nitrosoguanidine (N-methyl-N'-nitro-N-nitrosoguanidine).

Inactivation of the gene can also be performed by conventional methods, such as a mutagenesis treatment using UV irradiation or nitrosoguanidine (N-methyl-N'-nitro-N-nitrosoguanidine), site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45), also called "Red-driven integration".

Methods for preparation of plasmid DNA, digestion and ligation of DNA, transformation, selection of an oligonucleotide as a primer, and the like may be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

2. Method

The method can be a method for producing a product of a reaction catalyzed by a protein having 2-oxoglutarate-dependent enzyme activity by cultivating the bacterium as described above in a culture medium containing a substrate of the reaction, and isolating the produced product from the medium.

According to the product and the specificity of the protein having 2-oxoglutarate-dependent enzyme activity, the substrate is suitably selected. For example, when the product is (2S,3R,4S)-4-hydroxy-L-isoleucine and the protein has L-isoleucine dioxygenase activity, the substrate may be L-leucine.

Thus, a method for producing (2S,3R,4S)-4-hydroxy-L-isoleucine by cultivating the bacterium as described herein in a culture medium containing L-isoleucine, and isolating produced (2S,3R,4S)-4-hydroxy-L-isoleucine from the medium can be used.

The medium chosen for the culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, can be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used. The medium can contain L-isoleucine (20-40 g/l).

The cultivation is preferably performed under aerobic conditions, such as a shaking culture, or a stirring culture with aeration, at a temperature of 20 to 40° C., or in another example 30 to 38° C. The pH of the culture is usually between 5 and 9, or in another example between 6.5 and 7.2. The pH of the culture can be adjusted with ammonia, calcium carbonate, various acids, various bases, and buffers.

Examples of separation and purification methods can include a method in which the (2S,3R,4S)-4HIL is contacted with an ion exchange resin to adsorb basic amino acids followed by elution and crystallization, and a method in which the product obtained by elution is discolored and filtrated with activated charcoal followed by crystallization to obtain (2S,3R,4S)-4HIL.

With respect to the product other than (2S,3R,4S)-4-hydroxy-L-isoleucine, the culture condition, the separation and purification methods and the line are similarly selected depending on the nature of the chosen bacterium and the target product.

EXAMPLES

The present invention will be explained in further detail with reference to the following examples; however, the invention is not limited thereto.

Example 1

Construction of the MG1655 [pELAC-IDO(Lys, 23)] and MG1655($P_L$-brnQ)[pELAC-IDO(Lys, 23)] Strains 1.1. Construction of the pMW119-IDO(Lys, 23) Plasmid.

An 0.8 kb DNA fragment of the chromosome of the *Bacillus thuringiensis* strain 2-e-2 was amplified using oligonucleotides SVS 170 (SEQ ID No:15) and SVS 169 (SEQ ID No:16) as a primers and purified chromosomal DNA as a template. The PCR protocol was as follows: initial cycle for 30 seconds at 94° C.; 4 cycles for 40 seconds at 94° C.; 30 seconds at 49° C.; 40 seconds at 72° C.; 35 cycles for 30 seconds at 94° C.; 30 seconds at 54° C.; 30 seconds at 72° C.

The PCR fragment was digested with BamHI and SacI endonucleases and then ligated into the pMW119 vector which had been previously treated with the same restrictases.

1.2. Construction of the pELAC-IDO (Lys, 23) Plasmid.

Figure 3:
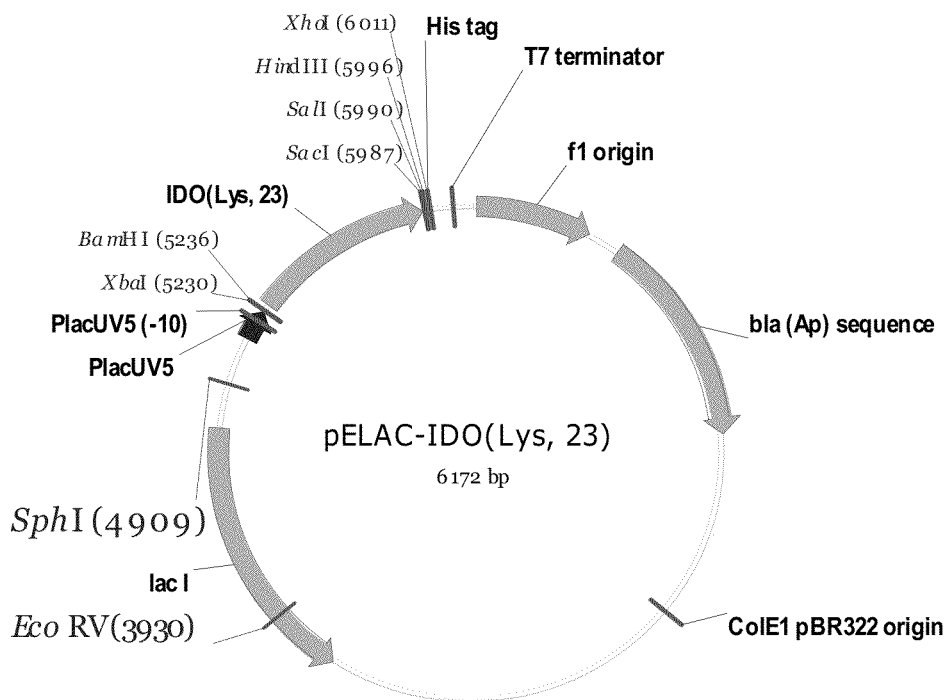
FIG. 3 shows the structure of the recombinant plasmid pELAC-IDO(Lys, 23).

A 0.76 kb DNA fragment was excised from the pMW119-IDO(Lys, 23) plasmid with the XbaI, SacI endonucleases, and then cloned into the pELAC-ilvA/XbaI-SacI vector (see Reference example 1), resulting in the recombinant plasmid pELAC-IDO (Lys, 23) (FIG. 3).

1.3. Construction of the MG1655 ($P_L$-brnQ) Strain.

The expression of the Ile-transporter BrnQ was increased in the MG1655 strain to improve the Ile influx. A 1.9 kbp DNA fragment harboring a Cm marker and the $P_L$-promoter was PCR-amplified using oligonucleotides SVS 179 (SEQ ID No:17) and SVS 180 (SEQ ID No:18) as primers and chromosomal DNA of the BW25113 cat-$P_L$-yddG (EP1449918A1, Russian patent RU2222596) strain as a template. Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1.9 kbp PCR product was obtained and purified in agarose gel and was used for electroporation of the *E. coli* strain MG1655 (ATCC 700926), which contains the plasmid pKD46 which has a temperature-sensitive replication origin. The plasmid pKD46 (Datsenko, K. A. and Wanner, B. L., Proc. Natl. Acad. Sci. USA, 2000, 97:12:6640-45) includes a 2,154 nucleotide DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655.

Electrocompetent cells were prepared as follows: *E. coli* MG1655/pKD46 was grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 µl of cells and ≈100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 µg/ml) and grown at 37° C. to select $Cm^R$ recombinants. Then, to eliminate the pKD46 plasmid, two passages on L-agar with Cm at 42° C. were performed and the obtained colonies were tested for sensitivity to ampicillin.

Figure 4:
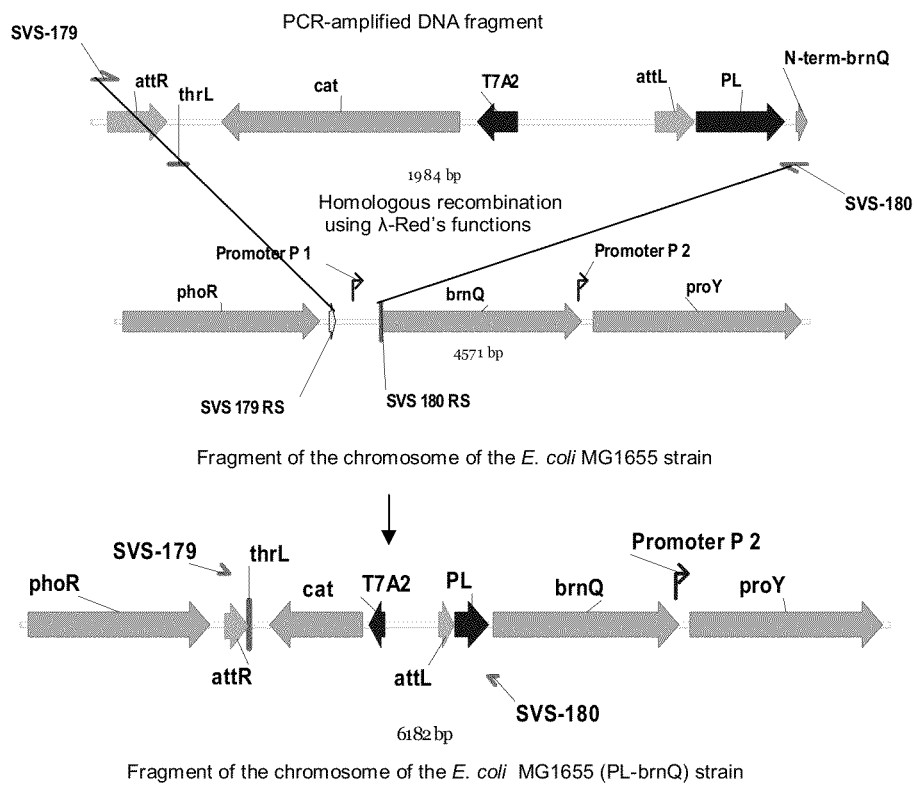
FIG. 4 shows the construction of the *E. coli* MG1655($P_L$-brnQ) strain.

Thus, the *E. coli* MG1655 ($P_L$-brnQ) strain was constructed (FIG. 4).

1.4. Construction of the MG1655 [pELAC-IDO(Lys, 23)] and MG1655($P_L$-brnQ)[pELAC-IDO(Lys, 23)] Strains.

The cells of the strains MG1655 and MG1655 ($P_L$-brnQ) were each transformed with plasmid pELAC-IDO (Lys, 23). Resulting clones were selected on a X-gal/IPTG agar-plate (blue/white test). Thus, the strains MG1655 [pELAC-IDO (Lys, 23)] and MG1655($P_L$-brnQ)[pELAC-IDO(Lys, 23)], respectively, were obtained.

Example 2

Production of 4HIL by *E. coli* Strain MG1655($P_L$-brnQ)[pELAC-IDO(Lys, 23)]

To test the effect of enhanced expression of a gene coding for L-isoleucine transporter on 4HIL production, cells of the MG1655 [pELAC-IDO(Lys, 23)] and MG1655($P_L$-brnQ) [pELAC-IDO(Lys, 23)] strains were grown in LB medium supplemented with ampicillin (200 µg/ml) and IPTG (1 mM) at 37° C. for about 4-5 hours. Specific IDO activity was measured in crude protein extracts for each grown recombinant *E. coli* strain as follows. Cells from 5 ml of culture were harvested by centrifugation at 4° C., re-suspended in 0.5 ml of buffer A*(50 mM TRIZMA, 5% glycerol, 1 mM EDTA, 1 mM DTT, pH 7 adjusted by HCl) and disrupted by sonication at 4° C. The reaction mixture (50 µl) contained 50 mM HEPES pH 7.0; 5 mM Ile; 0.5 mM α-ketoglutarate; 5 mM ascorbate; 5 mM $FeSO_4$ and an aliquot of the protein preparation. The reaction was incubated at 34° C. for 1 hour with shaking. 4HIL was detected using TLC or HPLC analysis as follows. TLC analysis: a thin-layer silica gel plate (10×15 cm) spotted with an aliquot (1-2 µl) of the reaction solution was developed with a developing solvent (2-propanol:acetone:ammonia:water=100:100:25:16) and 4HIL was detected with the ninhydrin reagent. HPLC analysis: High pressure chromatograph (Waters, USA) using a spectrofluorimeter 1100 series (Agilent, USA) was conducted. The chosen detection wave range: excitation wavelength at 250 nm, range of emission wavelengths were 320-560 nm. The separation by the accq-tag method was performed in a column Nova-Pak™ C18 150×3.9 mm, 4 µm (Waters, USA) at +40° C. The injection volume of the sample was 5 µl. The formation of amino acid derivatives and their separation was performed according to Waters manufacturer's recommendation (Liu, H. et al, J. Chromatogr. A, 828, 383-395 (1998); Waters accq-tag chemistry package. Instruction manual. Millipore Corporation, pp. 1-9 (1993)). To obtain amino acid derivatives with 6-aminoquinolyl-N-hydroxysuccinimidyl carbamate, the kit Accq-Fluor™ (Waters, USA) was used. The analysis by accq-tag method was performed using concentrated Accq-tag Eluent A (Waters, USA). All solutions were prepared using Milli-Q water, standard solutions were stored at +4° C. Results of measuring of IDO activity in crude extract of IDO-producing strains are shown in Table 1.

Cells of the MG1655 [pELAC-IDO(Lys, 23)] and MG1655($P_L$-brnQ)[pELAC-IDO(Lys, 23)] strains were harvested by centrifugation and re-suspended up to a final volume of 2 ml (to an $OD_{540}$≈0.03-0.04) in the medium MI30ch (50 mM $KH_2PO_4$ (pH7, adjusted by NaOH); 20 mM $NH_4Cl$, 2 mM $MgSO_4$, chalk—1.25 g/100 ml, 30 g/l Ile, 2 mM $FeSO_4$, 2 mM ascorbate, ampicillin 200 mg/l) supplemented with L-isoleucine and ketoglutarate, glucose or glycerol in various combinations (see Table 2, Table 3). Cells were cultivated for about 15 hours at 32° C. with vigorous agitation. Then, accumulation of 4HIL was investigated by HPLC-analysis as described above. The results of measuring the 4HIL produced by the MG1655 [pELAC-IDO(Lys, 23)] and MG1655($P_L$-brnQ)[pELAC-IDO(Lys, 23)] strains depending on the α-ketoglutarate, glucose, and glycerol are shown in Table 2 (at least 3 test tubes). The results of measuring the 4HIL produced by the MG1655 [pELAC-IDO(Lys, 23)] and MG1655($P_L$-brnQ)[pELAC-IDO(Lys, 23)] strains depending on the different concentrations of glycerol are shown in Table 3 (at least 3 test tubes). As follows from Table 2 and Table 3, MG1655($P_L$-brnQ)[pELAC-IDO(Lys, 23)] produced a higher amount of 4HIL, as compared with MG1655 [pELAC-IDO(Lys, 23)].

TABLE 1

| Strain | IDO activity (nmoles/min * mg) |
|---|---|
| MG1655 [pELAC-IDO(Lys, 23)] | 300 ± 12 |
| MG1655($P_L$-brnQ)[pELAC-IDO(Lys, 23)] | 280 ± 10 |

TABLE 2

| | Initial culture medium[a] | | | | Final culture broth |
|---|---|---|---|---|---|
| Strain | Ile (mM) | KG[b] (mM) | Gluc. (mM) | Glyc. (mM) | 4HIL (mM) |
| MG1655/ pELAC-IDO(Lys, 23) | 144 | 100 | 55 | 0 | 115 ± 6 |
| | | 0 | 55 | 0 | 17 ± 1 |
| | | 100 | 0 | 136 | 129 ± 6 |
| | | 0 | 0 | 136 | 77 ± 4 |
| MG1655($P_L$-brnQ)/ pELAC-IDO(Lys, 23) | | 100 | 55 | 0 | 128 ± 6 |
| | | 0 | 55 | 0 | 34 ± 2 |
| | | 100 | 0 | 136 | 131 ± 6 |
| | | 0 | 0 | 136 | 106 ± 5 |

[a] described in the text
[b] Abbreviations: KG, α-ketoglutarate; Gluc., glucose; Glyc., glycerol

TABLE 3

| | Initial culture medium[a] | | Final culture broth |
|---|---|---|---|
| Strain | Ile (mM) | Glycerol[b] (mM) | 4HIL (mM) |
| MG1655/ pELAC-IDO(Lys, 23) | 220 | 0 | 6 ± 0.3 |
| | | 136 | 86 ± 4 |
| | | 272 | 146 ± 7 |
| | | 408 | 164 ± 8 |
| MG1655($P_L$-brnQ)/ pELAC-IDO(Lys, 23) | | 0 | 7 ± 0.4 |
| | | 136 | 93 ± 5 |
| | | 272 | 158 ± 8 |
| | | 408 | 203 ± 10 |

[a] described in the text

Example 3

Construction of the MG1655 (ΔsucAB, ΔaceAK, $P_L$-brnQ) [pELAC-IDO(Lys, 23)] Strain 3.1. Construction of the MG1655 (ΔsucAB) Strain.

To delete the sucAB genes, the following manipulations were carried out. A 1.8 kb DNA fragment containing a $Cm^R$-marker and the $P_{tac}$ promoter was amplified by PCR with oligonucleotides SVS-192 (SEQ ID No:19) and SVS-193 (SEQ ID No:20) as primers and chromosomal DNA of the MG1655(attR-Cm-attL-$P_{tac}$) strain (Katashkina J. I. et al., Molekularnaya biologiya(RU), v. 39, No. 5, 1-10 (2005)) as the template. Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1.8 kbp PCR product was obtained and purified in agarose gel and was used for electroporation of the *E. coli* strain MG1655, which contains the plasmid pKD46 having a temperature-sensitive replication origin.

Electroporation was performed as described above. Cells after electroporation were incubated with 1 ml of SOC medium at 37° C. for 2.5 hours and then were plated onto L-agar containing chloramphenicol (30 μg/ml) and grown at 37° C. to select $Cm^R$ recombinants. Then, to eliminate the pKD46 plasmid, two passages on L-agar with Cm at 42° C. were performed and the obtained colonies were tested for sensitivity to ampicillin.

Thus, the *E. coli* MG1655 (ΔsucAB) strain was constructed.

3.2. Construction of the MG1655 (ΔaceAK) Strain.

To delete the aceAK genes, the following manipulations were carried out. A 1.8 kb DNA fragment containing the $Km^R$-marker and $P_{tac}$ promoter was amplified by PCR with oligonucleotides SVS-199 (SEQ ID No:21) and SVS-200 (SEQ ID No:22) as primers and pMW118-(λattL-$Km^r$-λattR) (see Reference example 2) plasmid DNA as the template.

Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1.8 kbp PCR product was obtained and purified in agarose gel and was used for electroporation of the *E. coli* strain MG1655, which contains the plasmid pKD46 which has a temperature-sensitive replication origin.

Electroporation was performed as described above. Cells after electroporation were incubated with 1 ml of SOC medium at 37° C. for 2.5 hours, and then were plated onto L-agar containing kanamycine (20 μg/ml) and grown at 37° C. to select $Km^R$ recombinants. Then, to eliminate the pKD46 plasmid, two passages on L-agar with Km at 42° C. were performed and the obtained colonies were tested for sensitivity to ampicillin.

Thus, the *E. coli* MG1655 (Δ aceAK) strain was constructed.

3.3. Construction of MG1655 (ΔsucAB, ΔaceAK, $P_L$-brnQ) Strain.

To eliminate the chloramphenicol resistance marker from the strain MG1655 ($P_L$-brnQ), cells were transformed with the plasmid pMW118-int-xis ($Ap^R$) (WO2005/010175). $Ap^R$ clones were grown on LB agar plates containing 150 mg/l ampicillin at 30° C. Several tens of $Ap^R$ clones were picked up and tested for chloramphenicol sensitivity. The plasmid pMW118-int-xis was eliminated from the $Cm^S$ cells by incubation on LB agar plates at 42° C. The obtained strain was used for further construction.

DNA fragments from the chromosome of the *E. coli* MG1655(ΔsucAB) strain were transferred to the strain obtained after elimination of the chloramphenicol resistance marker from the strain MG1655 ($P_L$-brnQ) by P1 transduction (Miller, J. H. Experiments in Molecular Genetics, Cold Spring Harbor Lab. Press, 1972, Plainview, N.Y.). Thus, MG1655 (ΔsucAB, $P_L$-brnQ) strain was constructed. DNA fragments from the chromosome of the *E. coli* MG1655 (ΔaceAK) strain were transferred to the strain MG1655 (ΔsucAB, $P_L$-brnQ). Thus, the MG1655 (ΔsucAB, ΔaceAK, $P_L$-brnQ) strain was constructed.

The cells of the strain MG1655 (ΔsucAB, ΔaceAK, $P_L$-brnQ) were transformed with plasmid pELAC-IDO (Lys, 23). The resulting clones were selected on a X-gal/IPTG agar-plate (blue/white test). Thus, the strain MG1655 (ΔsucAB, ΔaceAK, $P_L$-brnQ) [pELAC-IDO(Lys, 23)] was obtained.

3.4. Investigation of the Growth of Strains MG1655, MG1655 (ΔsucAB, ΔaceAK, $P_L$-brnQ), MG1655 [pELAC-IDO(Lys, 23)], and MG1655 (ΔsucAB, ΔaceAK, $P_L$-brnQ) [pELAC-IDO(Lys, 23)].

Strains MG1655 and MG1655 (ΔsucAB, ΔaceAK, P$_L$-brnQ) were grown in the following cultivation media:

A—M9 salts+glucose (0.4%);
B—M9 salts+glucose (0.4%)+DAP, Met, Lys (40 mg/l of each);
C—M9 salts+glycerol (0.4%);
D—M9 salts+glycerol (0.4%)+DAP, Met, Lys (40 mg/l of each).

Figure 5:
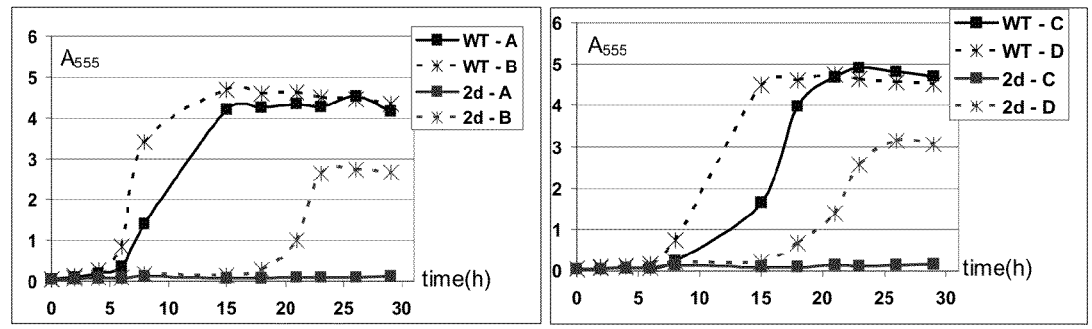
FIG. 5 shows the growth of the strains MG1655 and MG1655 (ΔsucAB, ΔaceAK, $P_L$-brnQ) on the M9-salts medium containing glucose or glycerol with or without addition of lysine, methionine, and diaminopimelate (DAP). Strains were grown in M9-salts medium supplemented with glucose or glycerol and, optionally, lysine, methionine and diaminopimelate (DAP). Abbreviations: Strains WT=MG1655; 2d=MG1655 (ΔsucAB, ΔaceAK, $P_L$-brnQ); Media: A=M9 salts+glucose; B=M9 salts+glucose+(Lys, Met, DAP); C=M9 salts+glycerol; D=M9 salts+glycerol+(Lys, Met, DAP).

The strains were cultivated in test tubes at 37° C. and optical density of the culture (A$_{555}$) was measured every hour. As it can be seen from FIG. 5, strain MG1655 (ΔsucAB, ΔaceAK, P$_L$-brnQ) lacks succinyl-CoA and cannot grow in the media A or C. Only the addition of lysine, methionine, and diaminopimelate (DAP) restored the growth of the strain.

Furthermore, the MG1655[pELAC-IDO(Lys, 23)] and MG1655 (ΔsucAB, ΔaceAK, P$_L$-brnQ) [pELAC-IDO(Lys, 23)] strains were grown in following media:

G—M9 salts+glucose (137 mM)
GI—M9 salts+glucose (137 mM)+L-isoleucine (137 mM)
Y—M9 salts+glycerol (136 mM)
YI—M9 salts+glycerol (136 mM)+L-isoleucine (137 mM)

Each medium contained ampicillin (100 mg/l). The strains were cultivated in test tubes at 37° C. and the optical density of the culture (A$_{555}$) was measured every hour.

Figure 6:
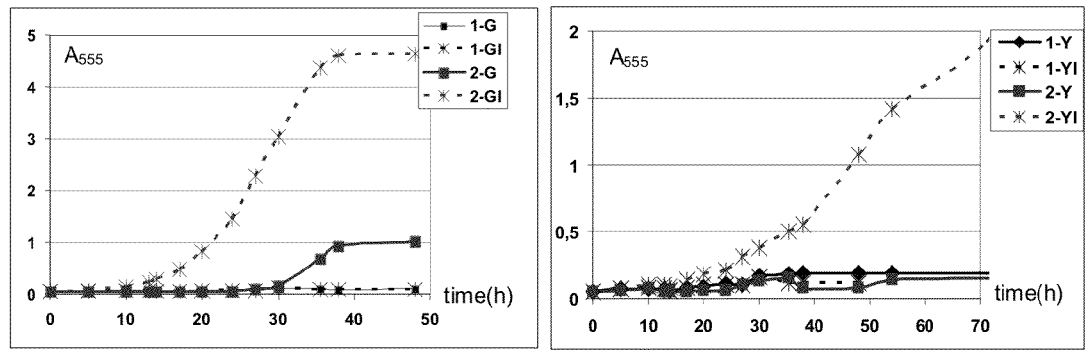
FIG. 6 shows the growth of the strains MG1655 [pELAC-IDO(Lys, 23)] and MG1655 (ΔsucAB, ΔaceAK, $P_L$-brnQ) [pELAC-IDO(Lys, 23)] on the M9-salts medium with or without addition of L-isoleucine. Abbreviations: Strains 1=MG1655[pELAC-IDO(Lys, 23)]; 2=MG1655 (ΔsucAB, ΔaceAK, $P_L$-brnQ) [pELAC-IDO(Lys, 23)]; Media: G=M9 salts+glucose (137 mM); GI=M9 salts+glucose (137 mM)+L-isoleucine (137 mM); Y=M9 salts+glycerol (136 mM); YI=M9 salts+glycerol (136 mM)+L-isoleucine (137 mM).

Expression of the IDO gene restored the growth of the MG1655 (ΔsucAB, ΔaceAK, P$_L$-brnQ) strain on the M9-salts medium supplemented with L-isoleucine (FIG. 6). This data demonstrates that isoleucine hydroxylation leads to the growth of the strain.

Example 4

Production of 4HIL by the *E. coli* Strain MG1655 (ΔsucAB, ΔaceAK, P$_L$-brnQ) [pELAC-IDO(Lys, 23)]

To test the effect of attenuated expression of genes coding for oxoglutarate dehydrogenase, isocitrate lyase, and isocitrate dehydrogenase phosphatase, cells of the MG1655(P$_L$-brnQ)[pELAC-IDO(Lys, 23)] and MG1655(ΔsucAB, ΔaceAK, P$_L$-brnQ)[pELAC-IDO(Lys, 23)] strains were each grown in medium A [(NH$_4$)$_2$SO$_4$—1.5 g/100 ml; KH$_2$PO$_4$—0.15 g/100 ml; MgSO$_4$—0.1 g/100 ml (MgSO$_4$.7H$_2$O—0.205 g/100 ml); Ile—220 mM; FeCl$_2$—2 mM, 1 mM IPTG, chalk—2 g/100 ml] supplemented with glucose (300 mM) or glycerol (500 mM) at 32° C. for 72 hours with vigorous agitation. Then, the accumulation of 4HIL was determined by HPLC-analysis as described above. The results of measuring the 4HIL produced by the MG1655(P$_L$-brnQ)[pELAC-IDO(Lys, 23)] and MG1655(ΔsucAB, ΔaceAK, P$_L$-brnQ) [pELAC-IDO(Lys, 23)] strains are shown in Table 4 (at least 3 test tubes). As follows from Table 4, MG1655(ΔsucAB, ΔaceAK, P$_L$-brnQ)[pELAC-IDO(Lys, 23)] produced a higher amount of 4HIL, as compared with MG1655(P$_L$-brnQ)[pELAC-IDO(Lys, 23)].

TABLE 4

| | Initial culture broth | | | Final culture broth |
|---|---|---|---|---|
| Strain | Glucose (mM) | Glycerol (mM) | Ile (mM) | 4HIL (mM) |
| MG1655(P$_L$-brnQ) [pELAC-IDO(Lys, 23)] | 300 | — | 220 | 134 |
| MG1655(Δ sucAB, Δ aceAK, P$_L$-brnQ)[pELAC-IDO(Lys, 23)] | 300 | — | 220 | 189 |
| MG1655(P$_L$-brnQ) [pELAC-IDO(Lys, 23)] | — | 500 | 220 | 100 |
| MG1655(Δ sucAB, Δ aceAK, P$_L$-brnQ)[pELAC-IDO(Lys, 23)] | — | 500 | 220 | 195 |

Example 5

Production of 4HIL by *E. coli* Strain MG1655 (ΔsucAB, ΔaceAK, P$_L$-brnQ)* [pEL-IDO(Lys, 23)]

5.1. Construction of the pEL-IDO(Lys, 23) Plasmid.

Due to the presence of the lacI gene in the pELAC-IDO (Lys, 23) plasmid, addition of IPTG is necessary to induce IDO expression during the biotransformation process of 4-HIL production. To avoid such IPTG-dependence, a large part of the lacI gene was deleted from pELAC-IDO(Lys, 23) plasmid (FIG. 1) by excision of the SphI-EcoRV DNA fragment using corresponding restrictases followed by ligation of the remaining part of the plasmid. Thus, the pEL-IDO(Lys, 23) plasmid was constructed.

5.2. Production of 4HIL

The MG1655 (ΔsucAB, ΔaceAK, P$_L$-brnQ)* strain was obtained by sequential excisions of Cm and Kn markers from the MG1655 (ΔsucAB, ΔaceAK, P$_L$-brnQ) strain using plasmid pMW118-int-xis (Ap$^R$) (WO2005/010175) as described above. Plasmids pELAC-IDO(Lys, 23) and pEL-IDO(Lys, 23) were introduced into resulted strain. Thus, the MG1655 (ΔsucAB, ΔaceAK, P$_L$-brnQ)* [pELAC-IDO(Lys, 23)] and MG1655 (ΔsucAB, ΔaceAK, P$_L$-brnQ)*[pEL-IDO(Lys, 23)] strains were obtained.

A piece of biomass of the MG1655 (ΔsucAB, ΔaceAK, P$_L$-brnQ)* [pELAC-IDO(Lys, 23)] or MG1655 (ΔsucAB, ΔaceAK, P$_L$-brnQ)*[pEL-IDO(Lys, 23)] strain from a freshly made LB-agar plate was separately inoculated in 50 ml of LB broth supplemented with Ap (100 mg/l) and cultivated at 37° C. for about 4 hours in 750 ml-flask. The obtained cell cultures were used as inoculums in the biotransformation carried out in "Marubischi" fermenters. The following cultivation parameters were used: starting culture volume—500 ml; agitation—1200 rev/min; air—1:1; cultivation temperature—34° C.; pH 7.0 was stabilized using 2.5 M NH$_4$OH.

An inoculum of the MG1655 (ΔsucAB, ΔaceAK, P$_L$-brnQ)* [pELAC-IDO] strain was added to 450 ml of medium containing (NH$_4$)$_2$SO$_4$—5 g/l; KH$_2$PO$_4$—1.5 g/l; MgSO$_4$7H$_2$O—1 g/l; FeSO$_4$7H$_2$O—0.01 g/l; isoleucine—22-23 g/l (≈170 mM); glucose—50 g/l; 1 mM IPTG (pH 7 adjusted by KOH, final volume=500 ml) and cultivated for about 20 hours.

An inoculum of the MG1655 (ΔsucAB, ΔaceAK, P$_L$-brnQ)* [pEL-IDO] strain was added to 450 ml of the above medium without IPTG and cultivated for about 20 hours. Concentrations of 4HIL and L-isoleucine were determined using HPLC analysis as above. As seen from the Table 5, the use of the pEL-IDO plasmid avoids dependence on IPTG.

TABLE 5

| Strain | Initial culture broth | | Final culture broth | | |
|---|---|---|---|---|---|
| | Glucose, (g/l) | Ile, (mM) | Glucose, (g/l) | Ile, (mM) | 4HIL, (mM) |
| MG1655(ΔsucAB, ΔaceAK, P$_L$-brnQ) [pELAC-IDO(Lys, 23)] | 50 | 179 | ND | ND | 132 |
| MG1655(ΔsucAB, ΔaceAK, P$_L$-brnQ) [pEL-IDO(Lys, 23)] | 50 | 174 | ND | 2.3 | 143 |

ND—non detected (≦0.1 g/l)

Reference Example 1

Construction of the pELAC-ilvA Plasmid

Figure 2:
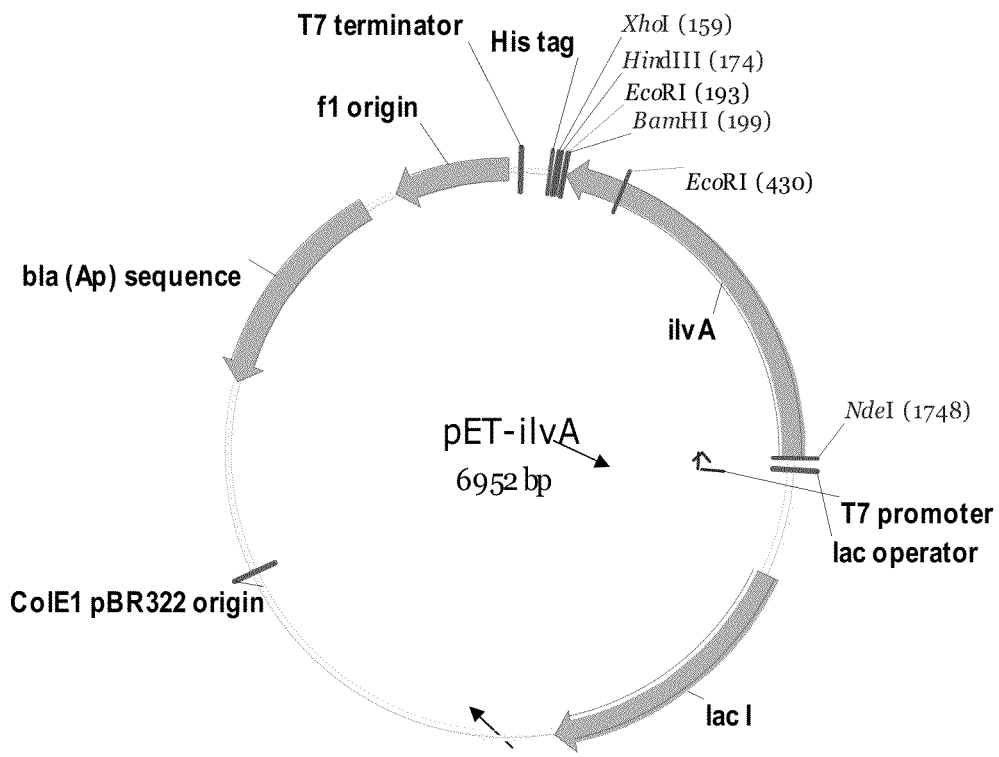
FIG. 2 shows the structure of the recombinant plasmid pET-IlvA.

The plasmid pET-ilvA was constructed as follows. A 1.5 kb fragment of the *E. coli* MG1655 strain chromosomal DNA was amplified using PCR with oligonucleotides ilvA-5 (SEQ ID NO: 23) and ilvA-3 (SEQ ID NO: 24) as primers. A piece of cell culture of the *E. coli* MG1655 strain from an LB-agar plate was used as the source of the template DNA for the PCR procedure. As a result, the DNA fragment contained the ilvA gene and was flanked by the NdeI and BamHI restriction sites. It was cloned into the pET22 (b+) vector (Novagen, Germany) between the NdeI-BamHI sites. Thus, recombinant plasmid pET-ilvA was constructed (FIG. 2).

The pELAC-ilvA plasmid was constructed from pET-ilvA by replacing the BglII-XbaI fragment containing the T7 promoter with the BglII-XbaI fragment containing the P$_{lac}$ promoter (SEQ ID NO: 25).

Reference Example 2

Construction of the pMW118-(λattL-Km$^r$-λattR) Plasmid

The pMW118-(λattL-Km$^r$-λattR) plasmid was constructed based on the pMW118-attL-Tc-attR (WO2005/010175) plasmid by substitution of the tetracycline resistance marker gene with the kanamycin resistance marker gene from the pUC4K plasmid (Vieira, J. and Messing, J., *Gene*, 19(3): 259-68 (1982)).

For that purpose, the large EcoRI-HindIII fragment from pMW118-attL-Tc-attR plasmid was ligated to two fragments from the pUC4K plasmid: HindIII-PstI fragment (676 bp) and EcoRI-HindIII fragment (585 bp).

Basic pMW118-attL-Tc-attR was obtained by ligation of the following four DNA fragments:
1) the BglII-EcoRI fragment (114 bp) carrying attL (SEQ ID NO: 26) which was obtained by PCR amplification of the corresponding region of the *E. coli* W3350 (containing λ prophage) chromosome using oligonucleotides P3 and P6 (SEQ ID NOS: 27 and 28) as primers (these primers contained the subsidiary recognition sites for BglII and EcoRI endonucleases);
2) the PstI-HindIII fragment (182 bp) carrying attR (SEQ ID NO: 29) which was obtained by PCR amplification of the corresponding region of the *E. coli* W3350 (containing λ prophage) chromosome using the oligonucleotides P5 and P6 (SEQ ID NOS: 30 and 31) as primers (these primers contained the subsidiary recognition sites for PstI and HindIII endonucleases);
3) the large BglII-HindIII fragment (3916 bp) of pMW118-ter_rrnB. The plasmid pMW118-ter_rrnB was obtained by ligation of the following three DNA fragments:
   a) the large DNA fragment (2359 bp) carrying the AatII-EcoRI fragment of pMW118 that was obtained in the following way: pMW118 was digested with EcoRI restriction endonuclease, treated with Klenow fragment of DNA polymerase I, and then digested with AatII restriction endonuclease;
   b) the small AatII-BglII fragment (1194 bp) of pUC19 carrying the bla gene for ampicillin resistance (Ap$^R$) was obtained by PCR amplification of the corresponding region of the pUC19 plasmid using oligonucleotides P7 and P8 (SEQ ID NOS: 32 and 33) as primers (these primers contained the subsidiary recognition sites for AatII and BglII endonucleases);
   c) the small BglII-PstIpol fragment (363 bp) of the transcription terminator ter_rrnB was obtained by PCR amplification of the corresponding region of the *E. coli* MG1655 chromosome using oligonucleotides P9 and P10 (SEQ ID NOS: 34 and 35) as primers (these primers contained the subsidiary recognition sites for BglII and PstI endonucleases);
4) the small EcoRI-PstI fragment (1388 bp) (SEQ ID NO: 36) of pML-Tc-ter_thrL bearing the tetracycline resistance gene and the ter_thrL transcription terminator; the pML-Tc-ter_thrL plasmid was obtained in two steps:
   the pML-ter_thrL plasmid was obtained by digesting the pML-MCS plasmid (Mashko, S. V. et al., Biotekhnologiya (in Russian), 2001, no. 5, 3-20) with the XbaI and BamHI restriction endonucleases, followed by ligation of the large fragment (3342 bp) with the XbaI-BamHI fragment (68 bp) carrying terminator ter_thrL obtained by PCR amplification of the corresponding region of the *E. coli* MG1655 chromosome using oligonucleotides P11 and P12 (SEQ ID NOS: 37 and 38) as primers (these primers contained the subsidiary recognition sites for the XbaI and BamHI endonucleases);
   the pML-Tc-ter_thrL plasmid was obtained by digesting the pML-ter_thrL plasmid with the KpnI and XbaI restriction endonucleases followed by treatment with Klenow fragment of DNA polymerase I and ligation with the small EcoRI-Van91I fragment (1317 bp) of pBR322 bearing the tetracycline resistance gene (pBR322 was digested with EcoRI and Van91I restriction endonucleases and then treated with Klenow fragment of DNA polymerase I).

Example 6

Production of Hydroxyl-Pro by the *E. coli* Strain MG1655 (ΔsucAB, ΔaceAK, $P_L$-brnQ)*

The synthesis of DNA of SEQ ID NO: 39 was consigned (Invitrogen), and a DNA encoding an amino acid sequence (SEQ ID NO: 40) of L-prolyl 4-hydroxylase from *Dactylosporangium* sp. was obtained in the form of a plasmid in which the DNA was ligated to BlueHeron pUCminusMCS. To the plasmid, sequences were inserted so that a sequence recognized by NdeI and a sequence recognized by HindIII were positioned at the 5' terminal and 3' terminal sides of the DNA, respectively, and the plasmid was digested with NdeI/HindIII. Separately, the ptrp4 vector (Journal of Molecular Catalysis B: Enzymatic 32 (2005)205-211) was digested with NdeI/HindIII. The two fragments digested with NdeI/HindIII were ligated, and introduced into the *E. coli* strain JM109 to obtain a transformant JM109/ptrp4_PDO.

Plasmid DNA was extracted from the obtained transformant, and introduced into the *E. coli* strain MG1655 and *E. coli* strain MG1655 (ΔsucAB, ΔaceAK, $P_L$-brnQ)* to obtain transformants MG1655/ptrp4_PDO and MG1655 (ΔsucAB, ΔaceAK, $P_L$-brnQ)*/ptrp4_PDO, respectively.

Strains MG1655/ptrp4_PDO and MG1655 (ΔsucAB, ΔaceAK, $P_L$-brnQ)*/ptrp4_PDO were cultivated in LB medium containing 100 mg/l ampicillin at 30° C. for 24 hours, and 300 μL of the culture was inoculated into 3 ml of LB medium containing 100 mg/l ampicillin and cultivated at 37° C. for 6 hours. To a test tube containing L-Pro and calcium carbonate so that their final concentrations were 10 g/l and 20 g/l, respectively, the obtained culture (0.3 ml) and the following cultivation media (2.7 ml) were added:

Medium Composition:

Medium A (300 ml): D-glucose (20 g/L), MgSO4.7H$_2$O (1 g/L);

Medium B (700 ml): ammonium sulfate (5 g/L), KH$_2$PO$_4$ (1.5 g/L), sodium ascorbate (0.01 g/L), FeSO$_4$7H$_2$O (0.1 g/L), adjusted pH to 7.0 with KOH.

Media A and B were separately autoclaved at 120° C. for 20 min, and mixed after cooling.

The D-glucose concentration (g/L) and the 4-hydroxyproline concentration (mM) are shown in Table 6. D-glucose was analyzed with a glucose analyzer (SAKURA SI, Japan). 4-Hydroxy-proline was analyzed by HPLC with Sumichiral OA-5000 (Sumika Analysis Center, Japan) (Mobile phase: 2 mM copper sulfate aqueous solution, column temperature: 30° C., flow rate: 1 ml/min, detection: UV 254 nm).

It was confirmed that MG1655 (ΔsucAB, ΔaceAK, $P_L$-brnQ)*/ptrp4_PDO could utilize D-glucose more efficiently for the production reaction of hydroxyproline compared with MG1655/ptrp4_PDO.

Example 7-1

Construction of *E. coli* Strain MG1655 (ΔsucA, ΔaceAK) and *E. coli* Strain MG1655 (ΔsucB, ΔaceAK)

To confirm whether the $P_L$-brnQ mutation is required for the efficient utilization of D-glucose or not, the following experiments were carried out.

To construct a strain deficient in 2-oxoglutarate dehydrogenase (sucA and sucB), isocitrate lyase (aceA) and isocitrate dehydrogenase kinase/phosphatase (aceK) without any mutation in $P_L$-brnQ, ΔaceAK was introduced into *E. coli* strain MG1655 ΔsucA strain (JW0715) and *E. coli* strain MG1655 ΔsucB strain (JW0716) of *E. coli* Keio Knockout Collection (http://ecoli.naist.jp) to obtain the *E. coli* strain MG1655 (ΔsucA, ΔaceAK) and *E. coli* strain MG1655 (ΔsucB, ΔaceAK). A deficiency of one of sucA and sucB results in the deficiency of 2-oxoglutarate dehydrogenase activity.

To delete the aceAK genes, the following manipulations were carried out. A 1.6 kb DNA fragment containing the $Cm^R$-marker was amplified by PCR with oligonucleotides SVS-199 (SEQ ID NO:21) and SVS-200 (SEQ ID NO:22) as primers and pMW118-(λattL-Cmr-λattR) (WO2005/010175) plasmid DNA as the template.

Conditions for PCR were as follows: denaturation step for 3 min at 94° C.; profile for 30 cycles: 30 sec at 94° C., 30 sec at 50° C., 2 min at 72° C.

A 1.6 kbp PCR product was obtained and purified in agarose gel and was used for electroporation of the *E. coli* strain MG1655 (ΔsucA), *E. coli* strain MG1655 (ΔsucB), which contains the plasmid pKD46 (WO2005/010175) which has a temperature-sensitive replication origin.

Electroporation was performed as described above. Cells after electroporation were incubated with 1 ml of SOC medium at 37° C. for 1 hour and then were plated onto L-agar containing Cm (25 μg/ml) and grown at 37° C. to select for $Cm^R$ recombinants. Then, to eliminate the pKD46 plasmid, two passages on L-agar with Cm at 42° C. were performed and the obtained colonies were tested for sensitivity to ampicillin.

After that, the $Cm^R$-marker was removed using plasmid pMW118-int-xis-ts ($Ap^R$) (WO2005/010175) as described above.

Thus *E. coli* strain MG1655 (ΔsucA, ΔaceAK) and *E. coli* strain MG1655 (ΔsucB, ΔaceAK) strain were constructed.

TABLE 6

| Strain | 0 min | | 22 hr | | 66 hr | |
|---|---|---|---|---|---|---|
| | Glucose, (g/l) | Pro** (mM) | Glucose, (g/l) | Hydroxy-Pro | Glucose, (g/l) | Hydroxy-Pro |
| MG1655/ptrp4_PDO | 18 | 87 | 7 | 15 | 0 | 31 |
| MG1655 (Δ sucAB, Δ aceAK, PL-brnQ)*/ | 18 | 87 | 11 | 15 | 3 | 58 |

**calculated value

Example 7-2

Production of 4HIL by *E. coli* Strain MG1655[pEL-IDO(Lys, 23)], *E. coli* Strain MG1655 (ΔsucA, ΔaceAK)[pEL-IDO(Lys, 23)], and *E. coli* Strain MG1655 (ΔsucB, ΔaceAK) [pEL-IDO(Lys, 23)]

The pEL-IDO(Lys, 23) plasmid was introduced into *E. coli* strain MG1655 as well as *E. coli* strain MG1655 (ΔsucA, ΔaceAK) and *E. coli* strain MG1655 (ΔsucB, ΔaceAK) obtained by the above method to obtain the transformants *E. coli* strain MG1655[pEL-IDO(Lys, 23)], *E. coli* strain MG1655 (ΔsucA, ΔaceAK)[pEL-IDO(Lys, 23)], and *E. coli* strain MG1655 (ΔsucB, ΔaceAK) [pEL-IDO(Lys, 23)].

These strains were cultivated in LB medium containing 100 mg/l ampicillin at 30° C. for 24 hours, and 300 μL of the culture was inoculated into 3 ml of LB medium containing 100 mg/l ampicillin and cultivated at 37° C. for 6 hours. To a test tube containing L-Ile and calcium carbonate so that their final concentrations are 10 g/l and 20 g/l, respectively, the obtained culture (0.3 ml) and the following cultivation media (2.7 ml) were added:

Medium Composition:

Medium A (300 ml): D-glucose (20 g/L), $MgSO_4 \cdot 7H_2O$ (1 g/L);

Medium B (700 ml): ammonium sulfate (5 g/L), $KH_2PO_4$ (1.5 g/L), sodium ascorbate (0.01 g/L), $FeSO_4 \cdot 7H_2O$ (0.1 g/L), adjusted pH to 7.0 with KOH.

The media A and B were separately autoclaved at 120° C. for 20 min, and mixed after cooling.

The remaining D-glucose and the produced 4-hydroxy-isoleucine in the medium are shown in Table 7. D-glucose was analyzed with a glucose analyzer (SAKURA SI, Japan). 4-Hydroxy-isoleucine was analyzed by HPLC with MCI GEL CRS10W (Mitsubishi Kagaku, Japan) (Mobile phase: 1 mM $CuSO_4$, 5% MeOH, column temperature: 30° C., flow rate: 1 ml/min, detection: UV 254 nm).

As a result, it was confirmed that in the reaction using *E. coli* strain MG1655 (ΔsucA, ΔaceAK)[pEL-IDO(Lys, 23)], and *E. coli* strain MG1655 (ΔsucB, ΔaceAK) [pEL-IDO(Lys, 23)] without the $P_L$-brnQ mutation, D-glucose could be more efficiently utilized for the conversion reaction by Ile dioxygenase compared with MG1655[pEL-IDO(Lys, 23)].

From these results, it is confirmed that strains deficient in the ΔsucAB, ΔsucA, ΔsucB, and ΔaceAK genes, such as *E. coli* MG1655 (ΔsucAB, ΔaceAK), *E. coli* MG1655 (ΔsucA, ΔaceAK), and *E. coli* MG1655 (ΔsucB, ΔaceAK), can be widely used for the 2-oxoglutrate-dependent enzymes.

3: brnQ gene from *E. coli*
4: BrnQ from *E. coli*
5: sucA gene from *E. coli*
6: SucA from *E. coli*
7: sucB gene from *E. coli*
8: SucB from *E. coli*
9: aceA gene from *E. coli*
10: AceA from *E. coli*
11: aceK gene from *E. coli*
12: AceK from *E. coli*
13: ilvE gene from *E. coli*
14: IlvE from *E. Coli*
15: primer SVS 170
16: primer SVS 169
17: primer SVS 179
18: primer SVS 180
19: primer SVS 192
20: primer SVS 193
21: primer SVS 199
22: primer SVS 200
23: primer IlvA-5
24: primer ilvA-3
25: BglII-XbaI fragment containing the $P_{lac}$ promoter
26: fragment attL
27: primer P3
28: primer P4
29: fragment attR
30: primer P5
31: primer P6
32: primer P7
33: primer P8
34: primer P9
35: primer P10
36: fragment of pML-Tc-ter_thrL
37: primer P11
38: primer P12
39: L-proline 4-hydroxylase gene from *Dactylosporangium* sp.
40: L-proline 4-hydroxylase from *Dactylosporangium* sp.

While the invention has been described in detail with reference to the preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of (2S,3R,4S)-4-hydroxy-L-isoleucine can be enhanced. This compound is useful as a component of pharmaceutical compositions with insulinotropic activity. Production of (2S,3R,4S)-4-hydroxy-L-isoleucine is enhanced by using a bacterium transformed with a DNA fragment containing a gene coding for a protein having L-isoleucine dioxygenase activity.

TABLE 7

| Strain | 0 min | | 48 hr | | | 96 hr | | |
|---|---|---|---|---|---|---|---|---|
| | Glucose, (g/l) | Ile, (mM) | Glucose, (g/l) | Ile, (mM) | 4HIL, (mM) | Glucose, (g/l) | Ile, (mM) | 4HIL, (mM) |
| MG1655 [pEL-IDO(Lys, 23)] | 18 | 38 | 0 | 35 | 10 | 0 | 34 | 9 |
| MG1655(Δsuc A, Δace AK) [pEL-IDO(Lys, 23)] | 18 | 38 | 14 | 45 | 1 | 0 | 17 | 26 |
| MG1655(ΔsucB, Δace AK) [pEL-IDO(Lys, 23)] | 18 | 38 | 14 | 44 | 1 | 0 | 26 | 17 |

EXPLANATION OF SEQUENCES

1: L-isoleucine dioxygenase gene from *Bacillus thuringiensis* strain 2-e-2
2: L-isoleucine dioxygenase from *Bacillus thuringiensis* strain 2-e-2

The invention claimed is:

1. A method for manufacturing a product of a reaction catalyzed by a protein having 2-oxoglutarate-dependent enzyme activity, comprising:
   A) cultivating a bacterium transformed with a DNA fragment comprising a gene coding for a protein having 2-oxo-glutarate-dependent enzymatic activity, wherein said bacterium has been modified to attenuate the expression of a gene coding for oxoglutarate dehydrogenase, in a culture medium containing a substrate of the reaction; and wherein said protein has L-isoleucine dioxygenase activity and catalyzes a reaction coupled with the formation of succinate from 2-oxoglutarate; and
   B) isolating the product, wherein said product is (2S,3R,4S)-4-hydroxy-L-isoleucine or a salt thereof.

2. The method according to claim 1, wherein said expression is attenuated by inactivating said genes coding for oxoglutarate dehydrogenase.

3. The method according to claim 1, wherein said bacterium has been modified to attenuate the expression of genes coding for oxoglutarate dehydrogenase and isocitrate lyase.

4. The method according to claim 3, wherein said expression is attenuated by inactivating said genes coding for oxoglutarate dehydrogenase and isocitrate lyase.

5. The method according to claim 1, wherein said bacterium has been modified to attenuate the expression of genes coding for oxoglutarate dehydrogenase, isocitrate lyase, and isocitrate dehydrogenase phosphatase.

6. The method according to claim 5, wherein said expression is attenuated by inactivating said genes coding for oxoglutarate dehydrogenase, isocitrate lyase, and isocitrate dehydrogenase phosphatase.

7. The method according to claim 1, wherein the bacterium belongs to a genus selected from the group consisting of *Escherichia, Pseudomonas, Corynebacterium, Arthrobacter, Aspergillus*, and *Bacillus*.

8. The method according to claim 1, wherein the bacterium is selected from the group consisting of *Escherichia coli, Arthrobacter simplex, Corynebacterium glutamicum, Arthrobacter globiformis, Arthrobacter sulfureus, Arthrobacter viscosus*, and *Bacillus subtilis*.

9. The method according to claim 6, wherein said bacterium has been modified to overexpress a gene coding for an *Escherichia coli* L-isoleucine transporter.

10. The method according to claim 1, wherein the culture medium contains a carbon source selected from the group consisting of a carbohydrate, and an alcohol.

11. The method according to claim 10, wherein said carbohydrate is glucose, and said alcohol is glycerol.

12. The method according to claim 1, wherein said protein is L-isoleucine dioxygenase.

* * * * *